US007723286B2

(12) United States Patent
Fehr et al.

(10) Patent No.: US 7,723,286 B2
(45) Date of Patent: May 25, 2010

(54) COMPOUNDS FOR A CONTROLLED RELEASE OF ACTIVE MOLECULES

(75) Inventors: Charles Fehr, Versoix (CH); Arnaud Struillou, Ferney-Voltaire (FR); José Galindo, Les Avanchets (CH)

(73) Assignee: Firmenich SA, Geneva (CH)

( * ) Notice: Subject to any disclaimer, the term of this patent is extended or adjusted under 35 U.S.C. 154(b) by 1699 days.

(21) Appl. No.: 10/852,754

(22) Filed: May 25, 2004

(65) Prior Publication Data

US 2004/0220074 A1    Nov. 4, 2004

Related U.S. Application Data

(63) Continuation of application No. PCT/IB02/05365, filed on Dec. 11, 2002.

(30) Foreign Application Priority Data

Dec. 13, 2001    (WO) .................. PCT/IB01/02520

(51) Int. Cl.
*A61K 8/18*    (2006.01)
(52) U.S. Cl. .................... 512/8; 512/25; 252/522; 252/132; 252/173
(58) Field of Classification Search .................. 512/25; 252/522
See application file for complete search history.

(56) References Cited

U.S. PATENT DOCUMENTS

| 3,819,712 | A |   | 6/1974 | Lamparsky et al. ......... 260/593 |
| 3,845,134 | A | * | 10/1974 | Helmlinger .................. 568/63 |
| 3,883,572 | A |   | 5/1975 | Helmlinger et al. ......... 260/455 |
| 3,900,520 | A |   | 8/1975 | Schenk et al. ............... 260/586 |
| 3,952,062 | A | * | 4/1976 | Lamparsky et al. ........... 568/42 |
| 4,065,408 | A | * | 12/1977 | Evers et al. ..................... 512/7 |
| 4,107,209 | A | * | 8/1978 | Wilson et al. .................. 568/42 |
| 4,154,693 | A | * | 5/1979 | Wilson et al. ............... 510/106 |
| 4,162,335 | A | * | 7/1979 | Wilson et al. ............... 426/271 |
| 4,209,025 | A | * | 6/1980 | Wilson et al. ............... 131/279 |
| 2003/0119712 | A1 | * | 6/2003 | Fehr et al. ...................... 512/1 |

FOREIGN PATENT DOCUMENTS

| DE | 32 28 289 A1 | 2/1984 |
| DE | 33 07 869 A1 | 9/1984 |
| GB | 1 602 747 | 11/1981 |
| WO | WO 84/00542 | 2/1984 |
| WO | WO 84/03508 | 9/1984 |

OTHER PUBLICATIONS

Mandai et al. Journal of Organic Chemistry, Japan, 1984, 49(18), 3403-6. New synthetic method for gamma-geraniol, boll weevil pheromone, and alfa-damascone . . . .*
Stéphane DE Lombaert et al., XP 002031790,"Synthesis and Phase-Transfer Mediated Alkylations Of 2-Diethylamino-4-Phenylsulfonyl-2- Butenenitrile An Efficient Homoenolate Equivalent", Tetrahedron Letters,vol. 25, No. 32, pp. 3475-3478 (1984).
Niklas A. Plobeck et al, XP-002279019, "Synthesis of 2(E), 4(E)-Dienamides and 2(E), 4(E)-Dienoates from 1, 3-Dienes via 2-Phenylsulfonyl 1, 3-Dienes", J. Org. Chem., vol. 56, pp. 4508-4512 (1991).
Gilbert A. Bryant et al., XP-002160253, "Structure-Activity Studies on the Retinal Rod Outer Segment Isoprenylated Protein Methyltransferase", J. Am. Chem. Soc., vol. 114, pp. 3966-3973 (1992).
Masao Shiozaki et al., XP-002279018, "Synthesis Of a 3-Ether Analogue Of Lipid A", Carbohydrate Research, vol. 222, pp. 69-82, Elsevier Science Publishers B.V., Amsterdam,(1991).
Keiko Mochizuki et al., XP-002953512, "The Structures of Bioactive Cyclodepsipeptides, Beauveriolides I and II, Metabolites of Entomopathogenic Fungi *Beauveria sp.*", The Chemical Society of Japan, Bull, Chem. Soc. Jpn., vol. 66, No. 10, pp. 3041-3046 (1993).
V. Prelog et al., XP-001109151, 281. "Veilchenriechstoffe., Ubereinige Oxo-tetrahydro-jonone", Helv. Chim. Acta, vol. 31, No. 2, , pp. 2135-2142, (1948).
B. Tilak et al., "Synthesis of Sulphur Heterocyclics: Part IV-Synthesis of Thianaphthalenium & Thiaphenanthrenium Perchlorates" Indian J. Chem., vol. 7, pp. 191-195 (1969).
P. Loiseau et al., "(Hydroxy-3 alkyl) phénylsulfures á activité normolipémiante", Pharma. Acta Helv., vol. 58, No. 4, pp. 115-119 1983).
Kay Brickmann et al., "[2,3] -Thia-Wittig Rearrangements Proceeding with Complete Inversion or with Partial Loss of Configuration at the Carbanionic Center", Chem. Ber. vol. 126, pp. 1227-1239 (1993).
Joëelie Vidal et al., "Use Of Alumina For Elimination Of Sulfinic Acid From β-Aryl-And β-Alkylsulfonyl Carbonyl Compounds", Tetrahedron Letters, vol. 27 No. 32, pp. 3733-3736 (1986).
O. Manickam et al., "Lithium Bis[(1R,5R)-3-aza-3-benzyl-1,5-diphenylpentan-1,5-diolato]-Aluminium—A New Heterobimetallic Catalyst for Michael Addition Reactions", Department of Chemistry, Indian Institute of Technology, Tetrahedron, vol. 55, pp. 2721-2736 (1999).
S. Torii et al., "Stereoselective Synthesis of (±)-Irones", J. Org. Chem., vol. 45, pp. 16-20 (1980).
Michael Hargreaves et al., "3-Mercaptodihydrocarvone (True Carvone Hydrosulphide) and (1S, 4S, 5S)-4,7,7-Trimethyl-6-thia-1,5-bicyelo-[3,2,1]-octan-3-one", Z. Naturforsch. B: Anorg. Chem. Org. Chem. vol. 33b, pp. 1535-1539 (1978).
Murat E. Niyazymbetov et al, "Electrosynthesis Of New Stereoisomers Of Alkyl-and Arylthio Derivatives Of Levoglucosenone", Tetrahedron Lecters,vol. 35, No. 19, pp. 3037-3040 (1994).

(Continued)

*Primary Examiner*—Mark Eashoo
*Assistant Examiner*—M. Reza Asdjodi
(74) *Attorney, Agent, or Firm*—Winston & Strawn LLP

(57) ABSTRACT

The present invention relates to the field of perfumery. More particularly, it concerns compounds comprising at least one β-oxy or β-thio carbonyl moiety capable of liberating a perfuming molecule such as, for example, an α,β-unsaturated ketone, aldehyde or carboxylic ester. The present invention concerns also the use of the compounds in perfumery as well as the perfuming compositions or perfumed articles comprising the invention's compounds.

16 Claims, No Drawings

OTHER PUBLICATIONS

Georges P-J. Hareau et al., "Synthesis of Optically Active 5-(*tert*-Butyldimethylsiloxy)-2-cyclohexenone and Its 6-Substituted Derivatives as Useful Chiral Building Blocks for the Synthesis of Cyclohexane Rings. Syntheses of Carvone, Penienone, and Penihydrone", J. Am.. Chem. Soc., vol. 121, pp. 3640-3650 (1999).

S Torii. et al., Alicyclic Terpenoids From Cyclocitral Phenyl Sulfides. I. Acid-Catalyzed Cyclization Of Geranyl, Phenyl Sulfides To Cyclocitral Derivatives. A Synthesis Of α-And β- Ionones, Chem. Lett., pp. 479-482 (1975).

Alim A. Sayed et al., "A novel synthesis of bicyclo (3.1.0.) hexane system from Carvone", Current Science, Department of Chemistry, Abeda Inamdar Senior College for Girls, Pune 411 001, India, pp. 1-3 (1999).

Isao Kuwajima et al., "Quaternary Ammonium Fluoride-Catalyzed Conjugate Addition of Thiols to C=C Double Bonds", Department of Chemistry, Tokyo Institute of Technology, Ookayama, Meguro-ku, Tokyo, 152, Japan, Communications, pp. 602-604 (1976).

S Torii. et al., "Alicyclic Terpenoids from Cyclocitryl Phenyl Sulfides. VI. Syntheses of β- Ionone Derivatives", Department of Industrial Chemistry, School of Engineering, Okayama University, Okayama 700, Notes, vol. 51, No. 3, pp. 949-950 (1978).

Charles Fehr et al., "Efficient Synthesis of Enantiomerically Pure α-Ionone from (R)- and (S)- α-Dam ascone", Helvetica Chimica Acta, vol. 75 pp. 1023-1027 (1992).

\* cited by examiner

COMPOUNDS FOR A CONTROLLED RELEASE OF ACTIVE MOLECULES

CROSS-REFERENCE TO RELATED APPLICATIONS

This application is a continuation of international application PCT/IB02/05365 filed Dec. 11, 2002, the entire content of which is expressly incorporated herein by reference thereto.

TECHNICAL FIELD

The present invention relates to the field of perfumery. More particularly, it concerns compounds comprising at least one β-oxy or β-thio carbonyl moiety capable of liberating an active molecule such as, for example, an α,β-unsaturated ketone, aldehyde or carboxylic ester. The present invention concerns also the use of the compounds in perfumery as well as the perfuming compositions or perfumed articles comprising the invention's compounds.

BACKGROUND ART

The perfume industry has a particular interest for compounds which are capable of prolonging the effect of active ingredients over a certain period of time, for example in order to overcome the problems encountered when using perfuming ingredients which are too volatile or have a poor substantivity. These compounds can be used in various applications, as for example in fine or functional perfumery. The washing of textiles is a particular field in which there is a constant quest to enable the effect of active substances, in particular perfumes, to be effective for a certain period of time after washing and drying. Indeed, many substances having fragrances which are particularly suitable for this type of application are, in fact, known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

Among the compounds of the present invention a few are known from the prior art. The compounds are 3-(phenylmethoxy)-1-(2,6,6-trimethyl-2-cyclohexen-1-yl)-1-butanone (by Fehr C et al. in Helv. Chim. Acta (1992), 75, 1023), 4-(phenylsulfonyl)-4-(2,6,6-trimethyl-1,3-cyclohexadien-1-yl)-2-butanone (by Torii S. et al. in Bull. Chem. Soc. Jpn. (1978), 51, 949), 4-(phenylthio)-4-(2,6,6-trimethyl-1-cyclohexen-1-yl)-2-butanone (by Kuwajima I. et al. in Synthesis (1976), 602), 4-(phenylsulfonyl)-4-(2,6,6-trimethyl-1 or 2-cyclohexen-1-yl)-2-butanone (by Torii S. et al. in Chem. Lett. (1975), 479), 2-methyl-5-(1-methylethenyl)-3-[(4-methylphenyl)sulfonyl]-cyclohexanone (by Sayed A. et al. in Curr. Sci. (1999), 77, 818), 2-methyl-5-(1-methylethenyl)-3-(phenylmethoxy)-cyclohexanone (by Hareau G. et al. in J. Am. Chem. Soc. (1999), 121, 3640), 2-methyl-5-(1-methylethenyl)-3-(octylthio)-cyclohexanone (by Niyazymbetov M. et al. in Tetrahedron Lett. (1994), 35, 3037), 3,3'-thiobis[2-methyl-5-(1-methylethenyl)-cyclohexanone (Hargreaves M et al. in Z. Naturforsch., B: Anorg. Chem., Org. Chem. (1978), 33B, 1535), 2-methyl-5-(1-methylethenyl)-3-(phenylthio)-cyclohexanone and its optical isomers (e.g. by Bakuzis P et al. in J. Org. Chem. (1981), 46, 235), 4-(phenylsulfonyl)-4-(2,5,6,6-tetramethyl-1 or 2-cyclohexen-1-yl)-2-butanone and their optical isomers (by Torii S. et al. in J. Org. Chem. (1980), 45, 16), beta-[(4-methylphenyl)thio]-benzenepropanal (by Manickam G. et al. in Tetrahedron (1999), 55, 2721), beta-[4-(trifluoromethyl)phenoxy]-benzenepropanal (in ES 2103680), beta-(phenylsulfonyl)-benzenepropanal (by Vidal J. et al. in Tetrahedron Lett. (1986), 27, 3733), beta-(phenylmethoxy)-benzenepropanal (by Brickmann K. et al. in Chem. Ber. (1993), 126, 1227), beta-[[[3,5-bis(1,1-dimethylethyl)-4-hydroxyphenyl]methyl]thio]-benzenepropanal (in EP 140298), beta-[(4-bromo-3-methylphenyl)thio]-benzenepropanal (by Loiseau P. et al. in Pharm. Acta Helv. (1983), 58, 115), beta-[(4-chlorophenyl)thio]-benzenepropanal (in FR 2509725), beta-[(4-methylphenyl)sulfonyl]-benzenepropanal (in WO 00/000198), and beta-(phenylthio)-benzenepropanal (e.g by Tilak B. et al. in Indian J. Chem. (1969), 7, 191).

All the compounds mentioned above have been used as synthetic intermediates, however, but not as perfuming ingredients. Moreover, in the documents mentioned hereinabove, there is no mention or suggestion of the potential use of the compounds as perfuming ingredients and more specifically of the use of such aid compounds to control the release of active, e.g. odoriferous, molecules.

SUMMARY OF THE INVENTION

We have, surprisingly, discovered the existence of monomeric, oligomeric, and polymer supported compounds comprising at least one β-oxy or β-thio carbonyl moiety that is capable of liberating an active molecule, namely an enone. As "active molecule" we mean here any molecule capable of bringing an odor benefit or effect into its surrounding environment, and in particular an odoriferous molecule, i.e., a perfuming ingredient, such as an α,β-unsaturated ketone, aldehyde or carboxylic ester. Accordingly, these compounds have a desired utility in perfuming compositions or perfumed articles as the active ingredient of such compositions and articles.

These compounds also can be used in various methods, such as to improve, enhance or modify the odor of a perfumed article or perfuming composition, for perfuming a surface, or for intensifying or prolonging the diffusion effect of an odoriferous ingredient on a surface. The following detailed description explains these uses and their attendant advantages over known compositions, articles and methods.

DETAILED DESCRIPTION OF THE PREFERRED EMBODIMENTS

The compounds of the present invention are defined by the formula

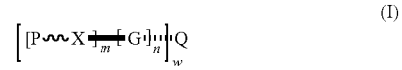

wherein:
a) w represents an integer from 1 to 10000;
b) n represents 1 or 0;
c) m represents an integer from 1 to 4;
d) P represents a hydrogen atom or a radical susceptible of generating an odoriferous α,β-unsaturated ketone, aldehyde or carboxylic ester and is represented by formula

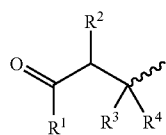

(II)

in which the wavy line indicates the location of the bond between the P and X;

$R^1$ represents a hydrogen atom, a $C_1$ to $C_6$ alkoxyl radical or a $C_1$ to $C_{15}$ linear, cyclic or branched alkyl, alkenyl or alkadienyl radical, optionally substituted by $C_1$ to $C_4$ alkyl groups; and $R^2$, $R^3$ and $R^4$ represent a hydrogen atom, an aromatic ring or a $C_1$ to $C_{15}$ linear, cyclic or branched alkyl, alkenyl or alkadienyl radical, optionally substituted by $C_1$ to $C_4$ alkyl groups; or two, or three, of the groups $R^1$ to $R^4$ are bonded together to form a saturated or unsaturated ring having 6 to 20 carbon atoms and including the carbon atom to which the $R^1$, $R^2$, $R^3$ or $R^4$ groups are bonded, this ring being optionally substituted by $C_1$ to $C_8$ linear, branched or cyclic alkyl or alkenyl groups; and with the proviso that at least one of the P groups is of the formula (II) as defined hereinabove;

e) X represents a functional group selected from the group consisting of the formulae i) to xiii):

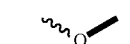 i)

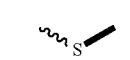 ii)

 iii)

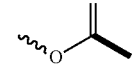 iv)

 v)

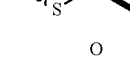 vi)

 vii)

 viii)

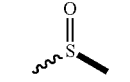 ix)

-continued

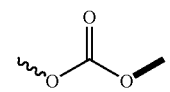 x)

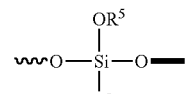 xi)

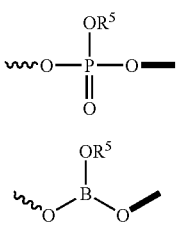 xii)

xiii)

in which formulae the wavy lines are as defined previously and the bold lines indicate the location of the bond between the X and G, and $R^5$ represents a hydrogen atom, a $C_1$ to $C_{22}$, saturated or unsaturated, alkyl group or an aryl group, optionally substituted by $C_1$ to $C_6$ alkyl or alkoxyl groups or halogen atoms; and with the proviso that X may not exist when P represents a hydrogen atom;

f) G represents a multivalent radical (with a m+1 valence) derived from an aryl radical, optionally substituted, or a divalent cyclic, linear or branched alkyl, alkenyl, alkadienyl or alkylbenzene hydrocarbon radical having from 6 to 22 carbon atoms, or a tri-, tetra- or pentavalent cyclic, linear or branched alkyl, alkenyl, alkadienyl or alkylbenzene hydrocarbon radical having from 1 to 22 carbon atoms, the hydrocarbon radical being optionally substituted and containing from 1 to 10 functional groups selected from the group consisting of ether, ester, ketone, amine, quaternary amines and amides; with optional substituents of G being halogen atoms, $NO_2$, $OR^6$, $NR^6_2$, $COOR^6$ or $R^6$ groups, $R^6$ representing a $C_1$ to $C_{15}$ alkyl or alkenyl group; and g) Q represents a hydrogen atom (in which case w=1 and n=1), or represents a group $[[P-X]_m[G]_n]$ wherein P, X, G, n and m are as defined previously (in which case w=1), or a dendrimer selected from the group consisting of the polyalkylimine dendrimers, amino acids (e.g. lysine) dendrimers, mixed amino/ether dendrimers and mixed amino/amide dendrimers, or a polysaccharide selected from the group consisting of cellulose, cyclodextrins and starches, or a cationic quaternized silicon polymer, such as the ABLIQUAT® (origin: Goldsmith, USA), or still a polymeric backbone derived from a monomeric unit selected from the group consisting of the formulae A) to E) and mixtures thereof:

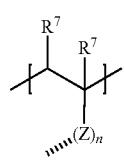 A)

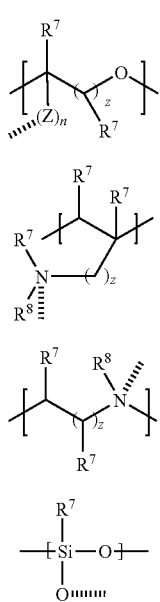

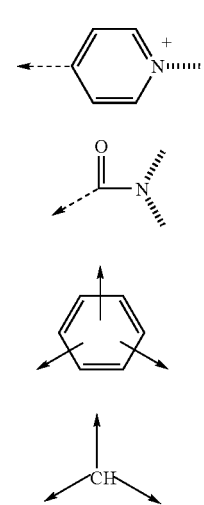

in which formulae the hatched lines indicate the location of the bond between the monomeric unit and G;

z represents an integer from 1 to 5;

n is defined as previously;

$R^7$ represents, simultaneously or independently, a hydrogen atom, a $C_1$-$C_{15}$ alkyl or alkenyl group, a $C_4$-$C_{20}$ polyalkylene glycol group or an aromatic group;

$R^8$ represents, simultaneously or independently, a hydrogen or oxygen atom, a $C_1$-$C_5$ alkyl or glycol or does not exist; and Z represents a functional group selected from the group consisting of the formulae 1) to 8), the branching units of the formulae 9) to 11), and mixtures thereof:

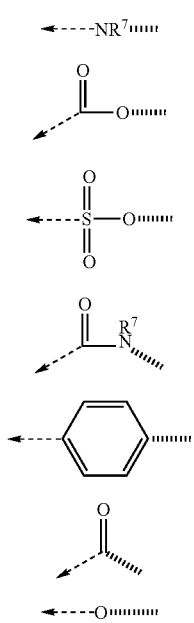

in which formulae the hatched lines are defined as previously, the dotted arrows indicate the location of the bond between the Z and the remaining part of the monomeric unit and the arrows indicate the location of the bond between the Z and either G or the remaining part of the monomeric unit, $R^7$ being as defined previously; and with the proviso that Z does not represent a group of formula 1), 3), and 7) if the monomeric unit is of formula B).

As "odoriferous α,β-unsaturated ketone, aldehyde or carboxylic ester", expression used in the definition of P, we mean here an α,β-unsaturated ketone, aldehyde or carboxylic ester which is recognised by a person skilled in the art as being used in perfumery as perfuming ingredient. In general, the odoriferous α,β-unsaturated ketone, aldehyde or carboxylic ester is a compound having from 8 to 20 carbon atoms, or even more preferably between 10 and 15 carbon atoms.

Preferred compounds of formula (I) are those wherein:

a) w represents an integer from 1 to 10000;

b) n represents 1 or 0;

c) m represents 1 or 2;

d) P represents a hydrogen atom or a radical of the formulae (P-1) to (P-11), in the form of any one of its isomers:

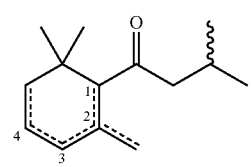

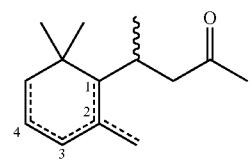

-continued (P-3)

(P-4)

(P-5)

(P-6)

(P-7)

(P-8)

(P-9)

(P-10)

(P-11)

in which formulae the wavy lines have the meaning indicated above and the dotted lines represent a single or double bond, $R^9$ indicating a methyl or ethyl group and $R^{10}$ representing a $C_6$ to $C_9$ linear or branched alkyl, alkenyl or alkadienyl group; and with the proviso that at least one of the P groups is of the formulae (P-1)) to (P-11) as defined hereinabove;

e) X represents a functional group selected from the group consisting of the formulae i)

ii)

iii)

iv)

vi)

viii)

ix)

x)

in which formulae the bold or wavy lines have the meaning indicated above; and with the proviso that X may not exist when P represents a hydrogen atom;

f) G represents a bivalent or trivalent radical derived from an aryl radical, optionally substituted, or a divalent cyclic, linear or branched alkyl, alkenyl, alkadienyl or alkylbenzene hydrocarbon radical having from 8 to 22 carbon atoms, or a trivalent cyclic, linear or branched alkyl or alkenyl hydrocarbon radical having from 1 to 22 carbon atoms, the hydrocarbon radical being optionally substituted and containing from 1 to 5 functional groups selected from the group consisting of ether, ester, ketone, amine, quaternary amines and amides; possible substituents of G are halogen atoms, $NO_2$, $OR^6$, $NR^6{}_2$, $COOR^6$ or $R^6$ groups, $R^6$ representing a $C_1$ to $C_{15}$ alkyl or alkenyl group; and g) Q represents a hydrogen atom (in which case w=1 and n=1), or represents a group $[[P-X]_m [G]_n]$ wherein P, X, G, n and m are as defined hereinabove (in which case w=1), or a polymeric backbone derived from a monomeric unit selected from the group consisting of the formulae A), C), D), E) and mixtures thereof:

A)

-continued

C)
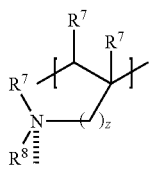

D)
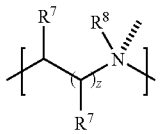

E)
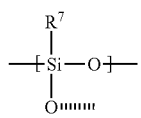

in which formulae the hatched lines, z and n are as defined previously;

$R^7$ represents, simultaneously or independently, a hydrogen atom, a $C_1$-$C_{10}$ alkyl group or a $C_4$-$C_{14}$ polyalkylene glycol group;

$R^8$ represents, simultaneously or independently, a hydrogen or oxygen atom, a $C_1$-$C_4$ alkyl or glycol or does not exist; and Z represents a functional group selected from the groups consisting of the formulae 1) to 5), 7), the branching units of the formulae 9) and 10), and mixtures thereof:

1)
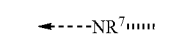

2)
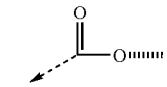

3)
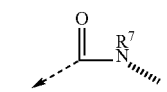

4)
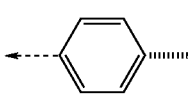

5)
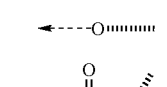

7)

9)

10)
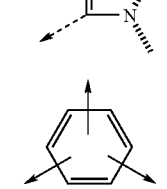

in which formulae the hatched lines, the dotted arrows and the arrows are defined as previously, $R^7$ being as defined hereinabove.

In a more preferred embodiment of the invention the compounds of formula (I) are those wherein:
a) w represents an integer from 1 to 10000;
b) n represents 1 or 0;
c) m represents 1 or 2;
d) P represents a radical of the formulae (P-1) to (P-11), as previously defined;
e) X represents a functional group selected from the group consisting of the formulae iii)
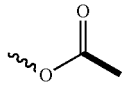

iv)
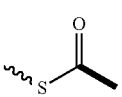

vi)
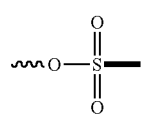

x)
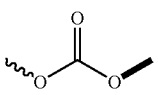

in which formulae the bold or wavy lines are defined as previously;

f) G represents a bivalent or trivalent radical derived from an aryl radical, optionally substituted, or a linear or branched alkyl, alkenyl, alkadienyl or alkylbenzene hydrocarbon radical having from 8 to 22 carbon atoms, the hydrocarbon radical being optionally substituted and containing from 1 to 5 functional groups selected from the group consisting of ether, ketone and amine; possible substituents of the G groups are halogen atoms, $NO_2$, $OR^6$, $NR^6_2$, $COOR^6$ or $R^6$ groups, $R^6$ representing a $C_1$ to $C_6$ alkyl or alkenyl group; and g) Q represents a hydrogen atom (in which case w=1 and n=1), or represents a group $[[P\text{-}X]_m[G]_n]$ wherein P, X, G, n and m are as defined hereinabove (in which case w=1), or a polymeric backbone derived from a monomeric unit selected from the group consisting of the formulae A), C), E) and mixtures thereof:

A)
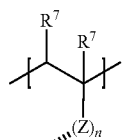

C)
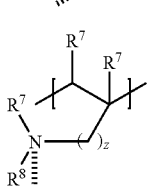

-continued

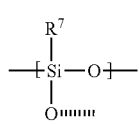
E)

in which formulae the hatched lines, z and n are as defined previously;

$R^7$ represents, simultaneously or independently, a hydrogen atom, a $C_1$-$C_5$ alkyl group or a $C_4$-$C_{10}$ polyalkylene glycol group;

$R^8$ represents, simultaneously or independently, a hydrogen or oxygen atom, a $C_1$-$C_4$ alkyl or glycol or does not exist; and Z represents a functional group selected from the groups consisting of the formulae 1) to 5), the branching units of the formulae 9) and 10), and mixtures thereof:

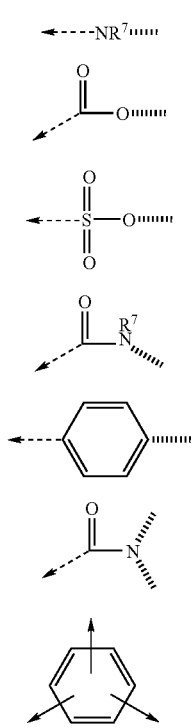

1)
2)
3)
4)
5)
9)
10)

in which formulae the hatched lines, the dotted arrows and the arrows are defined as previously, $R^7$ being defined as hereinabove.

Alternatively, in a more preferred embodiment of the invention, m represents 2, X represents a functional group of formula iii), as previously defined, and G represents a trivalent linear or branched alkyl or alkenyl hydrocarbon radical having from 1 to 7 carbon atoms, the hydrocarbon radical optionally containing from 1 to 5 functional groups selected from the group consisting of ether, ketone and amine.

In another alternative of a more preferred embodiment of the invention, m represents 1 or 2, X represents a functional group selected from the group consisting of formulae

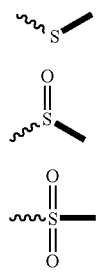
ii)
viii)
ix)

in which formulae the bold or wavy lines are defined as previously; and

G represents a bivalent radical derived from a linear or branched alkyl or alkenyl, hydrocarbon radical having from 8 to 20 carbon atoms, the hydrocarbon radical being optionally substituted and containing from 1 to 5 functional groups selected from the group consisting of ether, ketone and amine; possible substituents of the G groups are halogen atoms, $NO_2$, $OR^6$, $NR^6{}_2$, $COOR^6$ or $R^6$ groups, $R^6$ representing a $C_1$ to $C_6$ alkyl or alkenyl group.

It is understood that whereas m or w in formula (I) represents an integer greater than 1, then each of the various P may be identical or different, as well as each of the X or G.

An even more preferred embodiment of the present invention is represented by the compound of formula (I'):

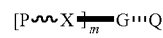

wherein m represents 1 or 2;

Q represents a hydrogen atom;

P represents a radical of the formulae (P-1) to (P-7), in the form of any one of their isomers:

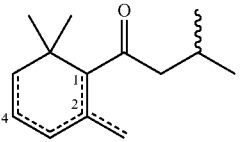
(P-1)

(P-2)

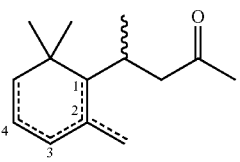
(P-3)

-continued

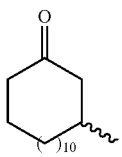
(P-4)

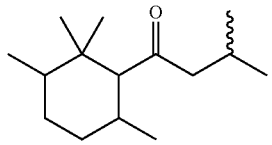
(P-5)

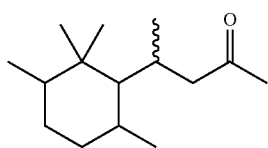
(P-6)

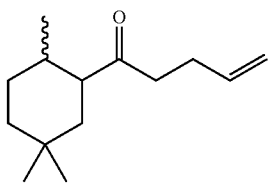
(P-7)

in which formulae the wavy lines and the dotted lines are as defined previously;

X represents a functional group selected from the group consisting of formulae

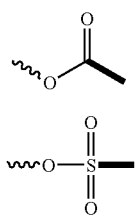

iii)

vi)

in which formulae the bold or wavy lines are defined as previously; and

G represents a bivalent or trivalent arene radical, optionally substituted by halogen atoms, $NO_2$, $OR^6$, $NR^6{}_2$, $COOR^6$ and $R^6$ groups, $R^6$ representing a $C_1$ to $C_6$ alkyl or alkenyl group.

Alternatively, the compounds of formula (I') are those wherein:

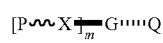
(I')

wherein P, m and Q are as defined hereinabove;

X represents a functional group of formula iii) or x), as defined above, and

G represents a bivalent radical derived from a linear or branched alkyl or alkenyl, hydrocarbon radical having from 8 to 15 carbon atoms; or G represents a trivalent radical derived from a linear or branched alkyl hydrocarbon radical having from 2 to 10 carbon atoms.

Yet, another alternative is represented by the compound of formula (I'):

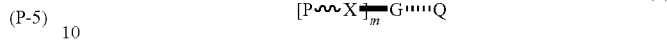
(I')

wherein P, m and Q are as defined hereinabove;

X represents a functional group selected from the group consisting of the formulae ii), viii) or ix), as defined above; and G represents a bivalent or trivalent radical derived from a linear or branched alkyl or alkenyl, hydrocarbon radical having from 8 to 15 carbon atoms.

The compound of formula (I'') represents also an even more preferred embodiment of the invention:

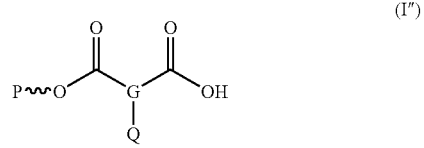
(I'')

wherein Q and P have the meaning given in formula (I'); and

G represents a trivalent radical derived from a linear or branched alkyl or alkenyl, hydrocarbon radical having from 3 to 6 carbon atoms.

Whereas m in formula (I') is equal to 2, then each of the various P may be identical or different, as well as each of the X.

The compounds of formula (I) may be synthesized from commercially available compounds by conventional methods. Generally speaking, the invention compounds are obtainable by the [1,4]-addition reaction between an odoriferous α,β-unsaturated ketone, aldehyde or carboxylic ester of formula (II')

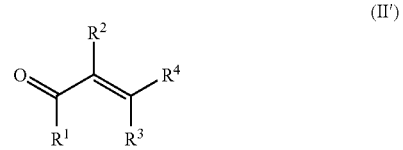
(II')

wherein the configuration of the carbon-carbon double bond can be of the E or Z type and the symbols $R^1$, $R^2$, $R^3$ and $R^4$ have the meaning indicated in formula (I); and a compound of formula $Q[(-G-)_n[-X-H]_m]_w$, wherein all the symbols have the meaning given in formula (I). For practical reasons, and according to the nature and nucleophilicity of the functional group X, the invention compounds may be more advantageously obtained by the reaction between the compound of formula (II''), which is the aldol derivative of the odoriferous compound of formula (II'),

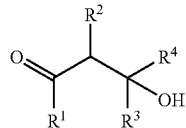

wherein the symbols $R^1$, $R^2$, $R^3$ and $R^4$ have the meaning indicated in formula (I); and a derivative of $Q[(-G-)_n[-X-H]_m]_w$ such as an acid chloride, a sulfonyl chloride or an alkyl chloro formate derivative.

The use of the aldol derivative is particularly interesting for the synthesis of all the compounds of formula (I) wherein X represents, e.g., a carboxylic, sulfonate, sulfate, carbonate, phosphate, borate, and silicate functional group. On the other hand, the direct use of the odoriferous molecule as starting material is particularly interesting for the synthesis of all the compounds of formula (I) wherein X represents, e.g., an ether, thioether or yet a thiocarboxylic derivative.

Polymeric materials may also be obtained by the polymerization of one monomer to which a moiety $(-G-)_n[-X-P]_m$ has been previously grafted. The polymerization may also be performed in the presence of other monomeric units bearing a different $(-G-)_n[-X-P]_m$ moiety.

General examples of this approach are illustrated in the following scheme, for particular cases of the compounds of formula (I):

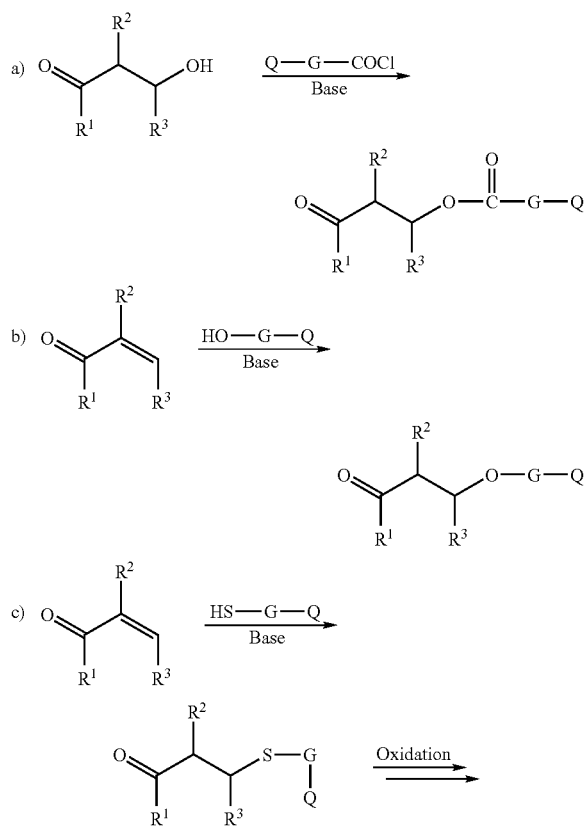

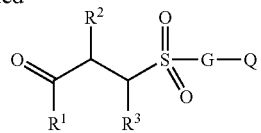

Although it is not possible to provide an exhaustive list of the compounds of formula $Q[(-G-)_n[-X-H]_m]_w$ which may be used in the synthesis of the invention compounds, one can cite as preferred examples the following: benzoic acid, 4- or 3-methyl-benzoic acid, 3- or 4-(N,N-dimethylamino)-benzoic acid, tosylic acid, benzenesulfonic acid, isophthalic acid, phthalic acid, terephthalic acid, benzene-1,2,3-tricarboxylic acid, ethylenediaminetetraacetic acid, nitrilotriacetic acid, alkyliminodiacetic acid (wherein alkyl represents a $C_1$ to $C_{10}$ alkyl group), 10-undecenoic acid, undecanoic acid, oxalic acid, malonic acid, succinic acid, glutaric acid, adipic acid, dodecanedionic acid, 1-octadecanethiol and $CH_3(CH_2)_{11}S(O)_aH$ (wherein a represent 0, 1 or 2). As polymeric compounds of formula $Q[(-G-)_n[-X-H]_m]_w$ one can cite also various polymethacrylate or polystyrene based polymers or co-polymers. As derivative of the compounds of formula $Q[(-G-)_n[-X-H]_m]_w$ one can cite their alkaline salts, the acid chloride (if X=COO), the sulfonyl chloride and sulfate chloride (if X=$SO_2$ or $SO_4$) and the chloro formate derivatives (if X=OCOO).

Similarly, it is not possible to provide an exhaustive list of the currently known odoriferous compounds of formula (II') which can be used in the synthesis of the invention compounds and subsequently be released. However the following can be named as preferred examples: alpha-damascone, beta-damascone, gamma-damascone, delta-damascone, alpha-ionone, beta-ionone, gamma-ionone, delta-ionone, beta-damascenone, 3-methyl-5-propyl-2-cyclohexen-1-one, 1(6),8-P-menthadien-2-one, 2,5-dimethyl-5-phenyl-1-hexen-3-one, 1-(5,5-dimethyl-1-cyclohexen-1-yl)-4-penten-1-one, 8 or 10-methyl-alpha-ionone, 2-octenal, 1-(2,2,3,6-tetramethyl-1-cyclohexyl)-2-buten-1-one, 4-(2,2,3,6-tetramethyl-1-cyclohexyl)-3-buten-2-one, 2-cyclopentadecen-1-one, nootkatone, cinnamic aldehyde, 2,6,6-trimethyl-bicyclo[3.1.1]heptane-3-spiro-2'-cyclohexen-4'-one, ethyl 2,4-decadienoate, ethyl 2-octenoate, methyl 2-nonenoate, ethyl 2,4-undecadienoate and methyl 5,9-dimethyl-2,4,8-decatrienoate. Of course, the aldol derivatives of formula (II'') of the latter compounds are also useful in the synthesis of the invention compounds.

Amongst the odoriferous compounds cited in the list hereinabove, the preferred are: the damascones, ionones, beta-damascenone, 1-(5,5-dimethyl-1-cyclohexen-1-yl)-4-penten-1-one, 1(6),8-P-menthadien-2-one, 2-cyclopentadecen-1-one, 1-(2,2,3,6-tetramethyl-1-cyclohexyl)-2-buten-1-one, 4-(2,2,3,6-tetramethyl-1-cyclohexyl)-3-buten-2-one and 2-cyclopentadecen-1-one.

As can be noticed from formula (I), the compounds of the invention are composed of three main parts, namely the release moiety P-X, the fragment G and the terminal group Q.

The special feature of the invention resides in the structure of the releasing moiety P-X. Owing to the particular chemical structure of the moiety, the compounds of formula (I) are capable of releasing, via a decomposition reaction, a residue and an odoriferous molecule such as, for example, an α,β-unsaturated ketone, aldehyde or carboxylic ester of formula (II').

An example of the decomposition reaction is illustrated in the following scheme:

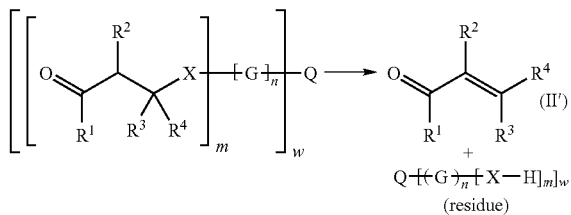

Q—[(G)$_n$—X—H]$_m$]$_w$
(residue)

The compound Q[(-G-)$_n$[-X-H]$_m$]$_w$, which is also the residue of the decomposition reaction, may be itself an odorless compound or a perfuming ingredient; preferably the residue is an odorless compound. Similarly, the compound of formula (I) is preferably odorless.

The nature of X plays an important role in the release kinetics of the odoriferous molecule. Thus, by a careful choice of the nature of X it is possible to tune the perfume release properties of the compounds of formula (I).

The second part of the compounds of the invention is the fragment G. Besides its role as a linker between the releasing unit P-X and Q, G can have also an influence in the releasing properties of the compounds of formula (I). Indeed, a shrewd choice of the chemical nature of the fragment, e.g. electron donating/withdrawing or hydrophobic/hydrophilic fragments, can allow to fine tune the perfume releasing properties.

The third component of the compounds of the invention is the terminal group Q. Whenever Q is not a hydrogen or a group [[P-X]$_m$[G]$_n$], the terminal group can play the role of a carrier to which can be attached several releasing units P-X. Moreover, depending on its specific nature, it can also play an important role in the effective deposition and surface substantivity of the molecules of the invention on the surface used for the application, especially on fabrics and hair. The role of a carrier in the effective deposition is well known by a person skilled in the art.

The decomposition reaction, which leads to the release of the odoriferous molecules, is believed to be influenced by pH changes or heat, but may be triggered by other types of mechanisms.

As the compounds of the invention are useful ingredients for the perfuming of various products, the present invention concerns also all different forms of the invention's compounds which can be advantageously employed in perfumery. Such forms include a composition of matter consisting of a compounds of formula (I) and a solvent commonly used in perfumery. As examples of the solvent, generally speaking, one can cite compounds such as dipropyleneglycol, diethyl phthalate, isopropyl myristate, benzyl benzoate, 2-(2-ethoxyethoxy)-1-ethanol or ethyl citrate, which are the most commonly used.

Additionally, the present invention concerns a perfuming composition comprising at least one compound of formula (I). Generally speaking, by "perfuming composition" we mean here a mixture comprising at least two perfuming ingredients, in any of their forms, and optionally one or more solvents commonly used in perfuming compositions. Therefore, a perfuming composition according to the invention comprises at least one invention's compound together with one or more perfuming co-ingredients and optionally one or more solvents.

The nature and type of these perfuming co-ingredients do not warrant a more detailed description here, which in any case would not be exhaustive, the skilled person being able to select them on the basis of its general knowledge and according to the nature of the product to be perfumed and the desired olfactory effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin. Many of these ingredients are in any case listed in reference texts such as the book of S. Arctander, Perfume and Flavor Chemicals, 1969, Montclair, N.J., USA, or its more recent versions, or in other works of a similar nature, as well as in the abundant patent literature in the field of perfumery.

Similarly, a detailed description of the nature and type of solvents commonly used in perfuming compositions cannot be exhaustive. A skilled person in the art is able to select them on the basis of the nature of the product to be perfumed. However, as non-limiting examples of such solvents, one can cite, in addition to the solvents mentioned above, also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

As previously mentioned, a compound of formula (I), in any of its forms, or a perfuming composition comprising the compound of formula (I), is a useful perfuming ingredient which can be advantageously used in all the fields of modern perfumery, such as fine perfumery or functional perfumery, as it enable a controlled release of odoriferous molecules.

Indeed, the invention compounds may be advantageously employed in fine or functional perfumery to achieve a more controlled deposition, and consequent release, of odoriferous compounds. For example, perfuming ingredients present as such in washing or perfuming compositions can have little staying-power on a surface and consequently be often eliminated, for example in the rinsing water or upon drying of the surface. This problem can be solved by using a compound of formula (I), for which we have been able to show that it possesses a surprising stability over storage and staying-power or tenacity on surfaces, such as textiles. Therefore, the compounds according to the invention, owing to a good substantivity, a low volatility and a controlled release of odoriferous molecules, can be incorporated in any application requiring the effect of rapid or prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin.

Thus, in perfumery, one of the major advantages of the invention resides in the fact that the compounds of formula (I) impart an intense fragrance to the treated surface, produced by an odoriferous molecule, which would not be detected on the surface over a sufficiently long period if the odoriferous α,β-unsaturated carbonyl derivative had been used as such, e.g., without a precursor.

Such a behavior makes the compounds of formula (I) particularly suitable as precursors of perfuming ingredients for applications associated with functional or fine perfumery. Consequently, the use of an invention's compound as perfuming ingredient is another object of the present invention. Moreover, perfumed articles comprising at least one invention's compound, in any of its forms, or a perfuming composition comprising the compound of formula (I), are also an object of the present invention.

Suitable perfumed articles comprise solid or liquid detergents and fabric softeners as well as all the other articles common in perfumery, namely perfumes, colognes or aftershave lotions, perfumed soaps, shower or bath salts, mousses, oils or gels, hygiene products or hair care products such as shampoos, body-care products, deodorants or antiperspirants, air fresheners and also cosmetic preparations. As detergents are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Preferred perfuming compositions or perfumed articles are perfumes, fabric detergents or softener bases.

Typical examples of fabric detergents or softener composition into which the compounds of the invention can be incorporated are described in WO 97/34986 or in U.S. Pat. Nos. 4,137,180 and 5,236,615 or EP 799,885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Some of the above-mentioned articles may represent an aggressive medium for the invention compounds, so that it may be necessary to protect the latter from premature decomposition, for example by encapsulation.

For the sake of clarity, it has to be mentioned that, by "perfumed article" we mean here a finished consumer product, or a part of the consumer product, capable of exerting a perfuming action. Therefore, a perfumed article according to the invention comprises at least a part of the whole formulation corresponding to the desired article, e.g. a detergent or a part of it, and at least an invention's compound optionally together with one or more perfuming co-ingredients and optionally one or more solvents.

The nature and type of the constituents of the article do not warrant a more detailed description here, which in any case would not be exhaustive, the skilled person being able to select them on the basis of its general knowledge and according to the nature and the desired effect of the article.

The proportions in which the compounds according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 5% by weight, or even more, of the compounds of the invention based on the weight of the composition into which they are incorporated. Concentrations lower than these, such as in the order of 0.01% to 1% by weight, can be used when these compounds are applied directly in the perfuming of the various consumer products mentioned hereinabove.

The present invention also relates to a method for the perfuming of a surface or to a method for intensifying or prolonging the diffusion effect of the characteristic fragrance of an odoriferous ingredient on a surface, characterized in that the surface is treated in the presence of a compound of formula (I). Suitable surfaces are, in particular, textiles, hard surfaces, hair and skin.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacement δ are indicated in ppm with respect to the TMS as standard, the coupling constants J are expressed in Hz. GPC analyses were performed on a Macherey-Nagel Nucleogel GPC 500-5 column (300×7.7 mm i.d.), eluted with THF at 0.5 ml/min and calibrated with commercially available standards (origin: Fluka).

Example 1

Synthesis of Compounds of Formula (I) by Using the Aldol Derivative of α-Damascone as Starting Material The starting material, namely the 3-hydroxy-1-(2,6,6-trimethyl-2-cyclohexen-1-yl)-1-butanone, has been obtained according to K. H. Schulte-Elte et al. in *Helv. Chim. Acta* 1973, 56, 310.

a) Synthesis of 1-methyl-3-oxo-3-(2,6,6-trimethyl-2-cyclohexen-1-yl)propyl benzoate To a solution of 3-hydroxy-1-(2,6,6-trimethyl-2-cyclohexen-1-yl)-1-butanone (4.00 g, 92% pure, 17.5 mmol), $NEt_3$ (3.2 ml, 22.85 mmol) and dimethylamino pyridine (DMAP) (400 mg) in $CH_2Cl_2$ (100 ml) was added benzoylchloride (2.43 ml, 20.94 mmol). The reaction medium was stirred for 65 h at room temperature. Then, the mixture was acidified with 5% aqueous HCl and extracted twice with ether and washed with water, saturated aqueous $NaHCO_3$ and then with saturated aqueous NaCl. Finally, the organic phases were dried over $Na_2SO_4$, concentrated at 50-60°/0.03 mbar) and purified by flash-chromatography over $SiO_2$ (cyclohexane/AcOEt=97:3). 4.25 g of product were thus obtained (yield: 73%).

MS: 192 (52), 123 (22), 105 (100), 81 (13), 77 (20), 69 (45).

$^1$H-NMR: 0.92/0.93/0.94 (3 s, 6H); 1.12-1.23 (m, 1H); 1.39/1.42 (d, J=6; 3 H); 1.59 (s, 3H); 1.65-1.80 (m, 1H); 1.95-2.20 (m, 2H); 2.60-2.83 (m, 2H); 3.02-3.20 (m, 1H); 5.50-5.63 (m, 2H), 7.36-7.45 (m, 2H), 7.48-7.57 (m, 1H), 7.96-8.04 (m, 2H).

$^{13}$C-NMR: 210.1 (s); 165.7 (s); 132.8 (d); 130.5 (s); 129.9 (s); 129.5 (2 d); 128.2 (2 d); 123.8 (d); 67.4/6 (d); 63.6/8 (d); 51.1 (t); 32.5 (s); 30.7/8 (t); 27.9 (q); 27.8 (q); 23.5 (q); 22.6 (t); 20.0/1 (q).

b) Synthesis of 1-methyl-3-oxo-3-(2,6,6-trimethyl-2-cyclohexen-1-yl)propyl 3-(dimethyl-amino)benzoate To a solution of 3-hydroxy-1-(2,6,6-trimethyl-2-cyclohexen-1-yl)-1-butanone (4.00 g, 92% pure, 17.5 mmol), 3-N,N-dimethylaminobenzoic acid (3.13 g, 19.0 mmol), and DMAP (1.85 g, 15.2 mmol) in $CH_2Cl_2$ (50 ml) was added N,N'-dicyclohexylcarbodiimide (DCC) (4.31 g, 20.9 mmol) in $CH_2Cl_2$ (15 ml). The reaction medium was stirred at room temperature for 70 h. Then, the mixture was acidified with concentrated HCl and extracted twice with ether and washed with water, saturated aqueous NaHCO$_3$ and then with saturated aqueous NaCl. Finally, the organic phases were dried over Na$_2$SO$_4$, concentrated at 50-60°/0.03 mbar) and purified by flash-chromatography over SiO$_2$ (cyclohexane/AcOEt=97:3). 4.20 g of product were thus obtained (yield: 68%).

MS: 357 (M$^+$, 19), 218 (8), 203 (28), 192 (13), 185 (10), 165 (19), 148 (100); 69 (36), 57 (19), 40 (51).

$^1$H-NMR: 0.92/0.93/0.94 (3 s, 6H); 1.12-1.23 (m, 1H); 1.38/1.40 (d, J=6; 3 H); 1.60 (s, 3H); 1.65-1.80 (m, 1H); 1.95-2.20 (m, 2H); 2.60-2.80 (m, 2H); 2.97 (s, 6H); 3.01-3.20 (m, 1H); 5.49-5.62 (m, 2H), 6.85-6.91 (m, 1H); 7.21-7.27 (m, 1H), 7.30-7.38 (m, 2H).

$^{13}$C-NMR: 210.0/2 (s); 166.3 (s); 150.4 (s); 131.1 (s); 129.9 (s); 128.9 (d); 123.8 (d); 117.5 (d); 116.7 (d); 113.3 (d); 67.3/5 (d); 63.6/8 (d); 51.1/2 (t); 40.6 (2 q); 32.4 (s); 30.7/8 (t); 28.0 (q); 27.8 (q); 23.5 (q); 22.6 (t); 20.0/1 (q).

c) Synthesis of bis[1-methyl-3-oxo-3-(2,6,6-trimethyl-2-cyclohexen-1-yl)propyl]terephthalate A solution of 3-hydroxy-1-(2,6,6-trimethyl-2-cyclohexen-1-yl)-1-butanone (3.55 g, 92% pure, 15.5 mmol) in CH$_2$Cl$_2$ (10 ml) was added to a solution of terephthaloylchloride (1.99 g, 9.80 mmol) and NEt$_3$ (2.12 g, 21.1 mmol) in CH$_2$Cl$_2$ (15 ml). The reaction medium was heated at reflux for 3 h. Then, the mixture was acidified with 5% aqueous HCl and extracted twice with ether and washed with water, 5% aqueous NaOH, again water and then with saturated aqueous NaCl. Finally, the organic phases were dried over Na$_2$SO$_4$, concentrated at 50-60°/0.03 mbar) and purified by flash-chromatography over SiO$_2$ (cyclohexane/AcOEt=9:1). 2.54 g of product were thus obtained (yield: 60%).

$^1$H-NMR: 0.91/0.94 (2 s, 12H); 1.12-1.23 (m, 2H); 1.40/1.43 (d, J=6; 6 H); 1.58 (s, 6H); 1.65-1.80 (m, 2H); 1.95-2.20 (m, 4H); 2.63-2.84 (m, 4H); 3.02-3.23 (m, 2H); 5.53-5.64 (m, 4H); 8.02 (s, 4H).

$^{13}$C-NMR: 209.9/210.0 (s); 164.9 (s); 134.2 (s); 129.7/8 (s); 129.4 (2 d); 123.9 (d); 67.9/68.1 (d); 63.6/8 (d); 51.0 (t); 32.5 (s); 30.7/8 (t); 28.0 (q); 27.8 (q); 23.5 (q); 22.6 (t); 20.0/1 (q).

d) Synthesis of 1-methyl-3-oxo-3-(2,6,6-trimethyl-2-cyclohexen-1-yl)propyl 4-methyl-benzenesulfonate To a solution of 3-hydroxy-1-(2,6,6-trimethyl-2-cyclohexen-1-yl)-1-butanone (1.00 g, 92% pure, 4.38 mmol), DMAP (100 mg), and NEt$_3$ (1.0 ml, 7.2 mmol) in CH$_2$Cl$_2$ (20 ml) was added, at 0° C., tosylchloride (2.02 g, 10.56 mmol). The reaction medium was stirred at room temperature for 4 days. Then, the mixture was acidified with concentrated HCl and extracted twice with ether and washed with water, saturated aqueous NaHCO$_3$ and then with saturated aqueous NaCl. Finally, the organic phases were dried over Na$_2$SO$_4$, concentrated at 50-60°/0.03 mbar). 0.76 g of product were thus obtained (yield: 50%).

MS (electrospray): 365 (M$^+$+1, 100), 353 (20), 279 (5), 228 (19), 193 (22).

$^1$H-NMR: 0.75/0.79/0.86/0.87 (4 s, 6H); 1.06-1.18 (m, 1H); 1.27/1.33 (d, J=6; 3 H); 1.49 (br, 3H); 1.52-1.65 (m, 1H); 1.93-2.15 (m, 2H); 2.43 (s, 3H); 2.55-3.08 (m, 3 H); 4.92-5.05 (m, 1H), 5.56 (br, 1H), 7.33 (d, J=8; 2 H), 7.77 (d, J=8; 2 H).

$^{13}$C-NMR: 209.5/6 (s); 144.6/7 (s); 133.6 (s); 129.7/8 (d); 129.4/6 (s); 127.9 (2 d); 124.0/1 (d); 75.6 (d); 63.5/8 (d); 51.3/6 (t); 32.3/4 (s); 30.6 (t); 27.7/8 (q); 27.7 (q); 23.3 (q); 22.5 (t); 21.6 (q); 21.0/1 (q).

e) Synthesis of 1-methyl-3-oxo-3-(2,6,6-trimethyl-2-cyclohexen-1-yl)propyl docecanoate Using the same experimental procedure as described in example 1.a), and using dodecanoyl chloride instead of benzoylchloride. The compound was obtained with 68% yield.

$^1$H-NMR: 0.82-0.95 (m, 9H); 1.17 (m, 1H); 1.20-1.35 (m, 19H); 1.59 (m, 5H); 1.79 (m, 1H); 1.95-2.18 (m, 2H); 2.22 (t, J=7, 2 H); 2.46-2.66 (m, 1H); 2.70 (m, 1H); 2.83-3.03 (m, 1H); 5.32 (m, 1H); 5.59 (b, 1H).

$^{13}$C-NMR: 210.0 (s); 173.0 (s); 129.9 (s); 123.8 (d); 66.6 (d); 63.7 (d); 50.9 (t); 34.6 (t); 32.5 (s); 31.9 (t); 30.7 (t); 29.1-29.6 (several t); 27.8/9 (q); 25.0 (t); 23.4 (q); 22.6/7 (t); 19.9/20.0 (q); 14.1 (q).

f) Synthesis of bis-[1-methyl-3-oxo-3-(2,6,6-trimethyl-2-cyclohexen-1-yl)propyl]succinate Using the same experimental procedure as described in example 1.b), and using succinic acid instead of 3-N,N-dimethylaminobenzoic acid. The compound was obtained with 51% yield.

$^1$H-NMR: 0.85-0.95 (m, 6H); 1.17 (m, 1H); 1.27 (t, J=8, 3 H); 1.58 (s, 3H); 1.70 (m, 1H); 1.95-2.20 (m, 2H); 2.22 (t, J=7, 2 H); 2.44-2.68 (m, 1H); 2.53 (s, 2H); 2.73 (b, 1H); 2.84-3.04 (m, 1H); 5.32 (m, 1H); 5.60 (b, 1H).

$^{13}$C-NMR: 210.1 (s); 171.4 (s); 129.8 (s); 123.8 (d); 66.2 (d); 63.7 (d); 50.8 (t); 32.4 (s); 30.7 (t); 29.8 (t); 27.8 (q); 23.4 (q); 22.6 (t); 19.9 (q).

g) 1-Methyl-3-oxo-3-(2,6,6-trimethyl-2-cyclohexen-1-yl)propyl 10-undecenoate

Using the same experimental procedure as described in example 1.b), and using 10-undecenoyl chloride instead of 3-N,N-dimethylaminobenzoic acid. The compound was obtained with 64% yield.

$^1$H-NMR: 0.83-0.96 (4 s, 6H); 1.17 (m, 1H); 1.20-1.45 (m, 15H); 1.58 (b, 3H); 1.70 (m, 1H); 1.95-2.17 (m, 4H); 2.22 (t, J=7; 2 H); 2.45-2.65 (m, 1H); 2.72 (m, 1H); 2.83-3.03 (m, 1H); 4.92 (m, 1H); 4.97 (m, 1H); 5.30 (m, 1H); 5.59 (m, 1H); 5.80 (m, 1H).

$^{13}$C-NMR: 210.0 (s); 172.9 (s); 139.2 (d); 129.8 (s); 123.8 (d); 114.1 (t); 66.6 (d); 63.7 (d); 50.95 (t); 34.5 (t); 33.8 (t); 32.4 (s); 30.7 (t); 28.9-29.3 (several t); 27.9 (q); 27.8 (q); 24.9 (t); 23.4 (q); 22.6 (t); 19.95 (q).

Example 2

Synthesis of the Compounds of Formula (I) by Using α-Damascone as Starting Material a) Synthesis of 3-[2-(dimethylamino)ethoxy-1]-(2,6,6-trimethyl-2-cyclohexen-1-yl)-1-butanone A solution of α-damascone (6.44 g; 33.5 mmol), N,N-dimethylaminoethanol (30.25 ml; 301 mmol) and tetramethylguanidine (TMG) (0.77 g; 6.70 mmol) was heated at 70° C. for 15 h. Afterward, the excess of N,N-dimethylaminoethanol was distilled at ca. 60° C./10 to 2 mbar. The crude product was diluted in diethyl ether (Et$_2$O) and this mixture was extracted with 5% aqueous HCl and washed with water and saturated aqueous NaCl. The combined aqueous phases were basified using aqueous NaOH and extracted twice with ether to recover the crude product in the organic phases. The organic phases were still washed with water and brine, then dried over Na$_2$SO$_4$ and concentrated. Bulb-to-bulb distillation of the crude product (100-125° C./0.05 mbar) afforded 2.94 g of the desired pure product (yield: 32%).

MS: 281 (M$^+$, 3), 192 (2), 123 (7), 73 (17), 72 (17), 58 (100).

$^1$H-NMR: 0.90/0.92/0.93 (3 s, 6H); 1.10-1.20 (m, 1H); 1.15/1.18 (d, J=6; 3 H); 1.58 (s, 3H); 1.65-1.77 (m, 1H); 1.95-2.20 (m, 2H); 2.23 (s, 6H); 2.37-2.56 (m, 3H); 2.70/2.75 (br, 1H); 2.82-3.00 (m, 1H); 3.40-3.50 (m, 1H); 3.55-3.64 (m, 1H); 3.86-3.99 (m, 1H); 5.58 (br, 1H).

$^{13}$C-NMR: 211.7/212.0 (s); 130.2 (s); 123.6 (d); 71.4/8 (d); 66.8/9 (t); 64.0/1 (d); 59.2 (t); 52.4/6 (t); 45.9 (2 q); 32.4 (s); 30.7/9 (t); 28.0 (q); 27.9 (q); 23.4/5 (q); 22.7 (t); 19.6/8 (q).

b) Synthesis of 3-(octadecylthio)-1-(2,6,6-trimethyl-2-cyclohexen-1-yl)-1-butanone A solution of α-damascone (1.00 g; 5.20 mmol), n-octadecylmercaptane (0.76 g; 2.66 mmol) and TMG (0.65 ml; 5.20 mmol) in THF (20 ml) was stirred at room temperature for 5 days. Afterward, the reaction medium was treated with 5% aqueous HCl, extracted twice with ether and washed with water, 5% aqueous NaOH and then with brine. Finally, the organic phases were dried over Na$_2$SO$_4$, concentrated at 90° C./0.04 mbar. 1.30 g of crude product were thus obtained (yield: 100% based on n-octadecylmercaptane).

MS (electrospray): 479 (M$^+$+1, 100), 401 (27), 356 (17), 313 (19).

$^1$H-NMR: 0.84-0.95 (4 peaks, 9H); 1.10-1.40 (m, ca. 34H); 1.50-1.62 (m, 5H); 1.67-1.80 (m, 1H); 1.95-2.18 (m, 2H); 2.48-2.95 (m, 5H); 3.27 (m, 1H); 5.59 (br, 1H).

$^{13}$C-NMR: 211.1/3 (s); 130.0 (s); 123.7 (d); 63.6/7 (d); 53.1/4 (t); 34.3/5 (d); 32.4/7 (s); 31.9 (t); 30.9/40.0 (t); 29.1-29.7 (many t); 27.8/28.0 (q); 27.8 (q); 23.5 (q); 22.6/7 (t); 21.6 (q); 14.1 (q).

Example 3

Synthesis of Compounds of Formula (I) by Using the Aldol Derivative of δ-Damascone as Starting Material The starting material, namely the 3-hydroxy-1-(2,6,6-trimethyl-3-cyclohexen-1-yl)-1-butanone, has been obtained according to U.S. Pat. No. 4,334,098.

General procedure: a solution of 3-hydroxy-1-(2,6,6-trimethyl-3-cyclohexen-1-yl)-1-butanone (124 mmol), NEt$_3$ (16.26 g (22.40 ml), 161 mmol) and DMAP (2 g) in CH$_2$Cl$_2$ (200 ml) was treated at room temperature with carboxylic chloride derivative (136 mmol). The reaction solution was stirred for 15 hours, treated with 5% HCl and extracted twice with ether, washed with H$_2$O, saturated aqueous NaHCO$_3$, then with brine, dried over Na$_2$SO$_4$, and concentrated at 65-75°/0.01 mbar. The oil was purified by flash-chromatography (cyclohexane/AcOEt=95:5), using SiO$_2$ (500 g).

a) 1-Methyl-3-oxo-3-(2,6,6-trimethyl-3-cyclohexen-1-yl)propyl benzoate

From benzoylchloride, in 76% yield.

MS: 192 (42), 122 (33), 105 (90), 77 (45), 69 (100).

$^1$H-NMR: 0.90 (2 d, 3H); 0.93-1.05 (4 s, 6H); 1.42 (2 d, 3H); 1.65-1.75 (m, 1H); 1.95-2.02 (2 b, 1H); 2.22-2.30 (m, 1H); 2.52 (m, 1H); 2.60-2.83 (m, 1H); 2.95-3.20 (m, 1H); 5.40-5.61 (m, 3H), 7.38-7.45 (m, 2H), 7.53 (m, 1H), 7.96-8.04 (m, 2 H).

$^{13}$C-NMR: 211.4 (s); 165.7 (s); 132.8 (d); 131.7 (d); 130.5 (s); 129.5 (2 d); 128.3 (2 d); 124.1 (d); 67.3 (d); 63.0 (d); 53.3 (t); 41.7 (t); 33.1 (s); 31.6 (d); 29.8 (q); 20.7 (q); 20.1 (q); 19.9 (q).

b) 1-Methyl-3-oxo-3-(2,6,6-trimethyl-3-cyclohexen-1-yl)propyl 10-undecenoate From 10-undecenoyl chloride, in 63% yield $^1$H-NMR: 0.88 (2 d, 3H); 0.98 (4 s, 6H); 1.22-1.42 (m, 13H); 1.58 (m, 2H); 1.65-1.75 (m, 1H); 1.92-2.05 (m, 3H); 2.22 (m, 3H); 2.50 (m, 1H); 2.42-2.58 (m, 1H); 2.78-3.02 (m, 1H); 4.92 (m, 1H); 4.97 (m, 1H); 5.33 (m, 1H); 5.45 (m, 1H); 5.53 (m, 1H); 5.80 (m, 1H).

$^{13}$C-NMR: 211.4 (s); 172.9 (s); 139.2 (d); 131.7 (d); 124.1 (d); 114.1 (t); 66.3 (d); 63.0 (d); 53.2 (t); 41.7 (t); 31.6-28.9 (many signals); 20.7 (q); 20.0 (q); 19.8 (q).

c) Tris-[1-Methyl-3-oxo-3-(2,6,6-trimethyl-3-cyclohexen-1-yl)propyl]1,3,5-benzene-tricarboxylate From 1,3,5-benzenetricarbonyl trichloride, using ClCH$_2$CH$_2$Cl as solvent, in 54% yield $^1$H-NMR (number of H: ×3): 0.87-1.10 (4 s+2 d, 9H); 1.38-1.47 (m, 3H); 1.65-1.75 (m, 1H); 1.93-2.04 (m, 1H); 2.28 (m, 1H); 2.52 (m, 1H); 2.60-2.88 (m, 1H); 2.95-3.23 (m, 1H); 5.45 (m, 1H); 5.54 (m, 1H), 5.66 (m, 1H); 8.72-8.78 (m, 1 H).

$^{13}$C-NMR: 211.3 (s); 164.1 (s); 134.3 (d); 131.6 (d); 131.4 (s); 124.2 (d); 68.2 (d); 63.1 (d); 53.2 (t); 41.7 (t); 33.1 (s); 31.6 (d); 29.8 (q); 20.1 (q); 20.0 (q); 19.9 (q).

d) Bis-[1-Methyl-3-oxo-3-(2,6,6-trimethyl-3-cyclohexen-1-yl)propyl]oxalate

From oxalylchloride, in 80% yield $^1$H-NMR (number of H: ×2): 0.90 (d, J=7, 3 H); 0.90-1.06 (4 s, 6H); 1.36 (2 d, 3H); 1.64-1.74 (m, 1H); 1.92-2.02 (2 b, 1H); 2.22 (m, 1H); 2.51 (m, 1H); 2.52-2.62 (m, 1H); 2.85-3.15 (m, 1H); 5.40-5.58 (m, 3H).

$^{13}$C-NMR: 210.7-211.1 (5 signals, s); 156.9 (s); 131.6 (d); 124.1 (d); 69.95 (d); 63.1 (d); 52.7 (t); 41.6 (t); 33.1 (s); 31.6 (d); 29.7 (q); 20.7 (q); 19.8 (q); 19.5 (q).

e) Bis-[1-Methyl-3-oxo-3-(2,6,6-trimethyl-3-cyclohexen-1-yl)propyl]dodecanedioate From the diacid chloride of dodecanedioate, in 59% yield $^1$H-NMR (number of H: ×2): 0.87/0.90 (d, J=7, 3 H); 0.92-1.03 (4 s, 6H); 1.27 (m, 9H); 1.58 (m, 2H); 1.70 (m, 1H); 1.96 (2 b, 1H); 2.22 (m, 3H); 2.43-3.02 (m, 3H); 5.34 (m, 1H); 5.45 (m, 1H); 5.53 (m, 1H).

$^{13}$C-NMR: 211.4 (s); 172.9 (s); 131.7 (d); 124.1 (d); 66.3 (d); 63.0 (d); 53.2 (t); 41.7 (t); 34.5 (t); 33.0 (s); 31.5 (d); 29.7 (q); 29.1-29.4 (several t); 25.0 (t); 20.7 (q); 19.9 (q); 19.8 (q).

f) Ethyl 1-methyl-3-oxo-3-(2,6,6-trimethyl-3-cyclohexen-1-yl)propyl carbonate A solution of 3-hydroxy-1-(2,6,6-trimethyl-3-cyclohexen-1-yl)-1-butanone (8.0 mmol) in pyridine (1.85 g, 23.4 mmol) was treated at 0° C. with ethyl chloroformate (1.24 g, 23.4 mmol). The reaction solution was stirred at room temperature for 36 hours, treated with 5% aqueous HCl and extracted twice with ether, washed (H$_2$O, saturated aqueous NaHCO$_3$, then brine), dried over Na$_2$SO$_4$ and concentrated. The oil (2.38 g) was purified by flash-chromatography (cyclohexane/AcOEt=98:2), using SiO$_2$ (100 g). Yield: 2.06 g (78%).

MS: 192(47); 177(10); 151(11); 123(55); 122(41); 107 (45); 91(11); 81(22); 69(100).

$^1$H-NMR: 0.89 (d, J=7, 3 H); 0.92-1.03 (4 s, 6H); 1.23-1.37 (m, 6H); 1.70 (m, 1H); 1.96 (m, 1H); 2.18-2.28 (m, 1H); 2.50 (m, 1.5H); 2.67 (m, 0.5H); 2.87 (m, 0.5H); 3.03 (m, 0.5H); 4.18 (m, 2H); 5.21 (m, 1H); 5.42-5.48 (m, 1H); 5.54 (m, 1H).

$^{13}$C-NMR: 211.4 (s); 154.4 (s); 131.7 (d); 124.2 (d); 70.5 (d); 63.8 (t); 63.1 (d); 53.1 (t); 41.7 (t); 33.1 (s); 31.6 (d); 29.7 (q); 20.7 (q); 20.0 (q); 19.8 (q); 14.3 (q).

Example 4

Synthesis of the Compounds of Formula (I) by Using δ-Damascone as Starting Material a) Synthesis of 3-(dodecylthio)-1-(2,6,6-trimethyl-3-cyclohexen-1-yl)-1-butanone A solution of δ-damascone (10.0 g; 52.1 mmol) and 1-dodecanthiol (8.42 g, 41.7 mmol) in THF (150 ml) was treated with DBU (7.92 g; 52.1 mmol) and stirred at 45° C. for 90 min. The reaction solution was treated with 5% aqueous HCl, extracted twice with ether, washed with H$_2$O, saturated aqueous NaHCO$_3$, then brine, dried over Na$_2$SO$_4$, and concentrated at 70° C./0.01 mbar. Yield of crude product: 16.2 g (99%).

$^1$H-NMR: 0.84-0.92 (m, 6H); 0.93-1.02 (4 s, 6H); 1.26 (m, 16H); 1.29 (m, 3H); 1.36 (m, 2H); 1.58 (m, 2H); 1.69 (m, 1H); 1.96 (2 b, 1H); 2.22 (m, 1H); 2.50 (m, 3.5H); 2.70 (m, 1H); 2.90 (m, 0.5H); 3.30 (m, 1H); 5.43 (m, 1H); 5.53 (m, 1H).

$^{13}$C-NMR: 212.4/5 (s); 131.8/9 (d); 124.1/2 (d); 62.9/63.0 (d); 55.2/3 (t); 41.7 (t); 34.1 (d); 33.0/2 (s); 31.9 (t); 31.6/8 (d); 30.9 (t); 29.8 (q); 29.0-29.8 (several t); 22.7 (t); 21.6/8 (q); 20.7 (q); 19.9 (q); 14.1 (q).

b) Synthesis of 3-(dodecylsulfinyl)-1-(2,6,6-trimethyl-3-cyclohexen-1-yl)-1-butanone A solution of 3-(dodecylthio)-1-(2,6,6-trimethyl-3-cyclohexen-1-yl)-1-butanone (2.00 g; 5.10 mmol) in MeOH (20 ml) was added at 0° C. to a solution of NaIO$_4$ (1.14 g, 5.30 mmol) in H$_2$O (11 ml). The temperature was brought to room temperature and EtOH (30 ml) was added. The suspension was stirred for 15 h and title compound extracted (ether/brine). The organic phase was washed with aqueous NaHSO$_3$, H$_2$O, saturated aqueous NaHCO$_3$, then brine, dried over Na$_2$SO$_4$, and concentrated. (16.2 g). Flash chromatography (cyclohexane/ethyl acetate=7:3, then 1:1) on SiO$_2$ (40 g) afforded 803 mg of the title compound (38%).

$^1$H-NMR: 0.85-0.94 (m, 6H); 0.95-1.03 (4 s, 6H); 1.25 (m, 19H); 1.45 (m, 2H); 1.65-1.83 (m, 3H); 1.97 (2 b, 1H); 2.28 (m, 1H); 2.46-2.62 (m, 2.5H); 2.67 (m, 1 H); 2.78 (m, 0.5H); 2.98 (m, 0.5H); 3.15-3.27 (m, 1.5H); 5.45 (m, 1H); 5.54 (m, 1H).

$^{13}$C-NMR: 211.8 (s); 131.5 (d); 124.3 (d); 62.9 (d); 49.1 (t); 48.0 (d); 41.6 (t); 33.2 (s); 31.9 (t); 31.8 (d); 29.8 (q); 29.0-29.8 (several t); 23.2 (t); 22.7 (t); 21.7 (q); 20.7 (q); 19.9 (q); 14.1 (q); 10.3/4 (q).

c) Synthesis of 3-(dodecylsulfonyl)-1-(2,6,6-trimethyl-3-cyclohexen-1-yl)-1-butanone A solution of KHSO$_5$ (62.1 mmol) in H$_2$O (50 ml) was added under ice cooling to a solution of 3-(dodecylthio)-1-(2,6,6-trimethyl-3-cyclohexen-1-yl)-1-butanone (5.00 g; 12.7 mmol) in MeOH (100 ml). The temperature was allowed to attain 40° C. The suspension was stirred for 2 hours and the title compound was extracted with ether/brine. The organic phase was washed with H$_2$O, saturated aqueous NaHCO$_3$, then brine, dried over Na$_2$SO$_4$, and concentrated. Flash chromatography (cyclohexane/ethyl acetate=95:5) on SiO$_2$ (130 g) afforded 2.59 g of product (48%).

$^1$H-NMR: 0.84-0.92 (m, 6H); 0.95-1.02 (3 s, 6H); 1.26 (m, 16H); 1.38 (m, 3H); 1.43 (m, 2H); 1.72 (m, 1H); 1.85 (m, 2H); 1.98 (2 b, 1H); 2.29 (m, 1H); 2.52 (m, 1H); 2.60 (m, 0.5H); 2.83 (m, 0.5H); 2.95 (t, J=8, 2 H); 3.12 (m, 0.5H); 3.35 (m, 0.5H); 3.63 (m, 1H); 5.46 (m, 1H); 5.55 (m, 1H).

$^{13}$C-NMR: 210.7 (s); 131.4 (d); 124.4 (d); 63.1 (d); 52.1 (d); 50.2 (t); 45.8 (t); 41.6 (t); 33.2 (s); 28.6-32.1 (several signals); 22.7 (t); 21.6 (t); 20.7 (q); 19.9 (q); 14.5/6 (q); 14.1 (q).

Example 5

Synthesis of the Compounds of Formula (I) by Using Other Perfuming Ingredients as Starting Material a) Synthesis of cis-4,4-dimethyl-2-(4-pentenoyl)cyclohexyl benzoate Ethyl vinyl ether (10.5 g) were added slowly and dropwise to 50 ml of Et$_2$O containing 6-carbomethoxy-4,4-dimethyl-cyclohexan-1-ol (25 g) at 0° C. under nitrogen. After 30 minutes the mixture was washed with saturated aqueous NaHCO3. After distillation (Bp 110-120° C./10 torr) were obtained 34 g of 2-carbomethoxy-4,4-dimethyl-1-(2-methyl-1,3-dioxapent-1-yl)cyclohexane (yield 98%)

$^1$H-NMR: 0.87-2.10 (18H); 2.35-2.80 (1H); 3.20-3.80 (5H); 4.00-4.30 (1H); 4.50-4.90 (1H).

A solution of 2-carbomethoxy-4,4-dimethyl-1-(2-methyl-1,3-dioxapent-1-yl) cyclohexane (5.16 g) in 10 ml of THF was added dropwise, over 15 minutes, to a solution of vinyl-magnesium bromide (1.2 g) and vinyl bromide (5.35 g) in 20 ml of THF at 65° C. After 4 hours the mixture was cooled and poured into cold 20% aqueous HCl (40 ml). Extraction of the mixture with Et$_2$O, removal of the solvents and a SiO$_2$ chromatography (CH$_2$Cl$_2$/AcOEt) provide pure 1-(2-hydroxy-5,5-dimethyl-1-cyclohexyl)-4-penten-1-one (yield 60%).

$^1$H-NMR: 0.96 (6H); 1.00-1.95 (6H); 2.20-2.80 (5H); 3.36 (1H); 4.19 (1H); 4.83-5.20 (2H); 5.83 (m, 1H)

Benzoyl chloride (12.8 g, 91 mmoles) was added dropwise to a stirred solution of 1-(2-hydroxy-5,5-dimethyl-1-cyclohexyl)-4-penten-1-one (16 g, 75 mmoles), Et$_3$N (10 g, 99 mmoles) and DMAP (1.8 g, 15 mmoles) in CH$_2$Cl$_2$ (380 ml) at 20° C. and under nitrogen. The solution was heated at 45° C. during 22 hours, cooled to room temperature and washed successively with 5% aqueous HCl, 10% aqueous Na$_2$CO$_3$, and again with water. The organic phase was dried over Na$_2$SO$_4$ and concentrated to afford a brown oil. Chromatography (SiO$_2$, AcOEt/Cyclohexane 1:9) and afforded 6.7 g of the title compound (yield=28%).

MS (electrospray): 314 (M$^+$+1, 1), 259 (5), 192 (14), 137 (39), 105 (100).

$^1$H-NMR: 0.96 (s, 3H); 1.06 (s, 3H); 1.25 (m, 1H); 1.50 (m, 2H); 1.82 (m, 1H); 1.90 (d.d., J=15.2 Hz, 1H); 2.05 (m, 1H); 2.27 (m, 2H); 2.59 (m, 2H); 2.74 (m, 1H); 4.86 (br.d., J=10 Hz, 1H); 4.95 (br.d., J=17 Hz, 1H); 5.68-5.78 (2H); 7.40 (m, 2H); 7.55 (m, 1H); 7.97 (m, 2H).

$^{13}$C-NMR: 209.1 (s); 165.6 (s); 137.1 (d); 133.0 (d); 130.3 (s); 129.6 (d); 128.4 (d); 115.2 (t); 69.5 (d); 49.5 (d); 39.6 (t); 34.8 (t); 33.0 (q); 32.8 (t); 29.9 (s); 27.6 (t); 26.7 (t); 23.9 (q).

b) Synthesis of 1-methyl-3-oxo-3-(2,2,C-3,T-6-tet-ramethyl-R-1-cyclohexyl)propyl benzoate 3-(Benzyloxy)-1-(2,2,C-3,T-6-tetramethyl-R-1-cyclohexyl)-1-butanone was obtained according a known procedure (C. Fehr, O. Guntern, *Helv. Chim. Acta* 1992, 75, 1023), in 56% yield.

MS: 210 (30), 167 (27), 139 (55), 124 (76), 91 (100), 83 (69), 69 (35).

$^1$H-NMR: 0.70-1.04 (m, 13H); 1.15-1.45 (m, 5H); 1.67 (m, 1H); 1.84 (m, 1H), 2.02 (m, 1H); 2.37 (m, 0.5H); 2.62 (m, 0.5H); 2.82 (m, 0.5H); 3.00 (m, 0.5H); 3.05 (s, 1H); 4.10 (m, 1H); 4.52 (m, 2H); 7.20-7.38 (m, 5H).

The treatment of a suspension of 82% pure benzylether (2.82 g, 7.30 mmol) and 10% Pd/C (282 mg) in EtOH (23 ml) was shaken in an H$_2$-atmosphere. After 5 hour the reaction mixture was filtered on Celite and concentrated. 3-hydroxy-1-(2,2,C-3,T-6-tetramethyl-R-1-cyclohexyl)-1-butanone was purified by flash-chromatography (cyclohexane/AcOEt=98:2, then 9:1), using SiO$_2$ (80 g). Yield: 969 mg (56%).

MS: 226 (5), 167 (18), 139 (57), 124 (28), 87 (25), 83 (100), 69 (55), 55 (26), 43 (26).

$^1$H-NMR: 0.73-1.04 (m, 13H); 1.15-1.45 (m, 6H); 1.70 (m, 1H); 1.85 (m, 1H), 2.03 (m, 1H); 2.41 (m, 0.5H); 2.53 (m, 0.5H); 2.64 (m, 0.5H); 2.74 (m, 0.5H); 3.30-3.65 (m, 1H); 4.22 (m, 1H).

The title compound was obtained from 3-hydroxy-1-(2,2,C-3,T-6-tetramethyl-R-1-cyclohexyl)-1-butanone and benzoylchloride using the same experimental procedure as described in example 1. a) in 51% yield.

MS: 208(18), 191(17); 167(32), 124(44), 105(100), 83(81), 77(28), 69(84), 55(23).

$^1$H-NMR: 0.73-0.86 (m, 9H); 0.93 (s, 3H); 0.93-1.05 (m, 1H); 1.15-1.35 (m, 2H); 1.41 (m, 4H); 1.66 (m, 1H); 1.84 (m, 1H), 2.05 (m, 1H); 2.79 (m, 1H); 2.96 (m, 1 H); 5.57 (m, 1H); 7.40 (m, 2H); 7.53 (m, 1H); 8.00 (m, 2H).

c) Synthesis of 3-oxocyclopentadecyl benzoate

Using the same experimental procedure as described in example 1.a) 3-oxocyclopentadecyl benzoate was obtained from 3-hydroxycyclopentadecanone and benzoylchloride in 80% yield.

MS: 344 (trace), 239 (7), 222 (47), 122 (36), 105 (100), 96 (26), 77 (34).

$^1$H-NMR: 1.18-1.48 (m, 18H); 1.55-1.88 (m, 4H); 2.50 (m, 2H); 2.86 (m, 2H); 5.48 (m, 1H); 7.43 (m, 2H); 7.55 (m, 1H); 8.03 (m, 2H).

$^{13}$C-NMR: 208.4 (s); 133.0 (d); 130.4 (s); 129.6 (2 d); 128.4 (2 d); 70.8 (d); 47.2 (t); 42.4 (t); 32.6 (t); 27.7 (t); 26.2-26.8 (7 t); 23.1 (t); 23.0 (t).

d) Synthesis of 1-methyl-3-oxo-3-(2,6,6-trimethyl-1,3-cyclohexadien-1-yl)propyl benzoate Using the same experimental procedure as described in example 1.a) the title compound was obtained from 3-hydroxy-1-(2,6,6-trimethyl-1,3-cyclohexadien-1-yl)-1-butanone and benzoylchloride in 60% yield.

$^1$H-NMR: 1.08 (2 s, 6H); 1.45 (d, 3H); 1.75 (s, 3H); 2.08 (m, 2H); 2.79 (m, 1H); 3.20 (m, 1H); 5.66 (m, 1H); 5.79 (m, 1H); 5.84 (m, 1H); 7.42 (m, 2H); 7.53 (m, 1 H); 8.02 (m, 2H).

$^{13}$C-NMR: 206.4 (s); 165.7 (s); 141.5 (s); 132.8 (d); 130.5 (s); 129.5 (2 d); 128.3 (2 d); 128.1 (d); 127.9 (d); 127.8 (d); 67.5 (d); 51.2 (t); 39.7 (t); 33.9 (s); 26.2 (q); 26.1 (q); 20.2 (q); 19.1 (q).

Example 6

Synthesis of Polymeric the Compounds of Formula (I) by Using δ-Damascone Derivatives as Starting Material a) 1-methyl-3-oxo-3-(2,6,6-trimethyl-3-cyclohexen-1-yl)propyl 4-vinylbenzoate A solution of DCC (3.60 g, 17.5 mmol) in 10 ml of CH$_2$Cl$_2$ was added to an ice-cold solution of 4-vinylbenzoic acid (2.35 g, 15.9 mmol), DMAP (1.55 g, 12.7 mmol) and 3-hydroxy-1-(2,6,6-trimethyl-3-cyclohexen-1-yl)-1-butanone (4.00 g, 19.1 mmol) in 30 ml of CH$_2$Cl$_2$. The reaction mixture was stirred at room temperature for 5 days. The precipitate was filtered off and the filtrate taken up in CH$_2$Cl$_2$, washed twice with 10% aqueous HCl, saturated aqueous Na$_2$CO$_3$ and saturated aqueous NaCl. The organic phases were dried over Na$_2$SO$_4$ and concentrated. Flash-chromatography over SiO$_2$ (heptane/ether 9:1) gave 4.02 g of the desired compound (yield: 74%).

MS: 193 (11), 192 (72), 177 (10), 149 (6), 148 (12), 135 (5), 132 (10), 131 (100), 124 (5), 123 (29), 122 (24), 121 (5), 108 (6), 107 (23), 103 (19), 102 (5), 91 (6), 81 (13), 79 (5), 77 (15), 69 (52), 41 (7).

$^1$H-NMR: 0.89 (d, J=7, 3 H); 0.93 (s, 3H); 1.02 (s, 3H); 1.41 (2 d, J=7, 6, 3 H); 1.70 (m, 1 H); 1.98 (m, 1H); 2.27 (t, J=10, 1 H); 2.50 (m, 1H); 2.63/3.00 (dd, J=18, 6, 1 H); 2.79/3.15 (dd, J=18, 7, 1 H); 5.37 (d, J=10, 1 H); 5.44 (m, 1H); 5.55 (m, 2 H); 5.85 (d, J=17, 1 H); 6.74 (dd, J=18, 11, 1 H); 7.44 (d, J=9, 2 H); 7.95 (d, J=8, 2 H).

$^{13}$C-NMR: 211.5 (s); 165.4 (s); 141.8 (s); 136.0 (d); 131.8 (d); 129.8 (d); 129.7 (s); 126.0 (d); 124.2 (d); 116.4 (t); 67.4/2 (d); 63.0 (d); 53.3 (t); 41.7 (2 t); 33.1 (2 s); 31.6 (2 d); 29.8 (q); 20.7 (q); 20.1 (q); 19.9 (q).

b) A random co-polymer of 1-methyl-3-oxo-3-(2,6,6-trimethyl-3-cyclohexen-1-yl)propyl 4-vinylbenzoate and 4-vinylbenzoic acid (ca 1:3)

A solution of 1-methyl-3-oxo-3-(2,6,6-trimethyl-3-cyclohexen-1-yl)propyl 4-vinylbenzoate (1.00 g, 2.9 mmol), 4-vinylbenzoic acid (1.30 g, 8.8 mmol) and 2,2'-azobisisobutyronitrile (AIBN) (0.10 g, 0.6 mmol) in 20 ml of dry THF was heated under N$_2$ at 80° C. for 2 days. Another 0.10 g of AIBN were added and, after 2 days, the reaction mixture was concentrated, the crude product redissolved in 3 ml of THF and precipitated with 4 ml of heptane (3×). Drying under high vacuum (0.3 mbar) gave 1.93 g of the desired compound (yield: 84%).

Average molecular weight (GPC): ca. 1700 g/mol.

IR (neat): 2925m (br.), 2870w, 2644w (br.), 2537w (br.), 1685s, 1606s, 1573m, 1508w, 1448w, 1419m, 1368m, 1311m, 1271s (br.), 1176s, 1101m, 1046m, 1016m, 936w, 882w, 854m, 800m, 774s, 705s, 684w, 670w.

$^{13}$C-NMR in THF-D$_8$: 211.6 (s, br.); 167.6 (s, br.); 165.7 (s, br.); 150.6 (s, br.); 132.7 (d); 130.6 (d, br.); 129.8 (s, br.); 128.4 (d, br.); 125.0 (d); 124.9 (d); 63.3 (d); 54.0 (t); 44.5 (t, br.); 42.5 (t); 41.7 (d, br.); 33.7 (s); 32.6 (d); 30.0 (q); 21.1 (q); 20.2 (q, br.).

c) 2-[2-(2-methoxyethoxy)ethoxy]ethyl 4-vinylbenzoate

As described in Example 6a) the compound was obtained by reacting together DCC (3.1 g, 14.9 mmol), 4-vinylbenzoic acid (2.0 g, 13.5 mmol), DMAP (1.3 g, 10.8 mmol) and 2-[2-(2-methoxyethoxy)ethoxy]ethanol (3.3 g, 20.3 mmol) for 2 days. Flash-chromatography over $SiO_2$ (heptane/ether gradient) and drying under high vacuum gave 3.1 g of a slightly yellow oil (yield: 78%).

MS: 176 (8), 175 (63), 174 (5), 148 (13), 132 (11), 131 (100), 103 (26), 102 (8), 89 (7), 87 (7), 77 (16), 59 (24), 58 (15), 45 (7).

$^1$H-NMR: 3.36 (s, 3H); 3.53 (m, 2H); 3.66 (m, 4H); 3.71 (m, 2H); 3.83 (m, 2H); 4.48 (m, 2H); 5.38 (d, J=11, 1 H); 5.86 (d, J=17, 1 H); 6.75 (dd, J=11, 18, 1 H); 7.45 (d, J=9, 2 H); 8.01 (d, J=8, 2 H).

$^{13}$C-NMR: 166.3 (s); 142.0 (s); 136.0 (d); 130.0 (d); 129.3 (s); 126.1 (d); 116.5 (t); 71.9 (t); 70.7 (t); 70.6 (t); 70.6 (t); 69.2 (t); 64.1 (t); 59.0 (q).

d) A random co-polymer of 1-methyl-3-oxo-3-(2,6,6-trimethyl-3-cyclohexen-1-yl)propyl 4-vinylbenzoate and 2-[2-(2-methoxyethoxy)ethoxy]ethyl 4-vinylbenzoate (ca. 1:2)

A solution of 1-methyl-3-oxo-3-(2,6,6-trimethyl-3-cyclohexen-1-yl)propyl 4-vinylbenzoate (0.29 g, 0.85 mmol) and of 2-[2-(2-methoxyethoxy)ethoxy]ethyl 4-vinylbenzoate (0.50 g, 1.7 mmol) in 5 ml of dry THF was rapidly added to a stirred solution of 0.05 g (0.3 mmol) of AIBN in 5 ml of dry THF under $N_2$. The reaction mixture was heated at 80° C. for 90 hours. After cooling down to room temperature, 1 ml of methanol was added and the mixture concentrated. The crude product was taken up in 2 ml of THF and extracted with 4-6 ml of heptane. The hexane phase was decanted and the procedure repeated twice. Concentration of the heptane phases and drying under high vacuum afforded 0.53 g of a highly viscous oil (yield: 67%).

Average molecular weight (GPC): ca. 8000 g/mol.

IR (neat): 3013w, 2922m, 2870m, 1710s, 1651w, 1607m, 1573w, 1507w, 1451m, 1418m, 1374m, 1365m, 1352m, 1307m, 1270s, 1197m, 1179m, 1135m, 1098s, 1029m, 1016m, 999w, 986w, 940m, 826w, 852m, 771m, 707s, 682m.

$^{13}$C-NMR: 211.7 (s, br.); 166.1 (s); 165.3 (s); 149.2 (s, br.); 131.7 (d); 129.6 (d, br.); 128.6 (d, br.); 128.1 (d, br.); 127.4 (d, br.); 124.3 (d); 124.2 (d); 71.9 (t); 70.6 (t); 70.6 (t); 69.2 (t); 67.3 (d, br.); 64.0 (t); 62.9 (d); 59.0 (q); 53.3 (t); 41.7 (t); 40.7 (d, br.); 33.1 (s); 31.6 (d); 29.8 (q); 20.7 (q); 20.1 (q); 19.9 (q).

e) A random co-polymer of 1-methyl-3-oxo-3-(2,6,6-trimethyl-3-cyclohexen-1-yl)propyl 4-vinylbenzoate and 2-[2-(2-methoxyethoxy)ethoxy]ethyl 4-vinylbenzoate (ca. 1:3)

As described in Example 6c) the polymer was obtained by reacting together 0.19 g (0.57 mmol) of 1-methyl-3-oxo-3-(2,6,6-trimethyl-3-cyclohexen-1-yl)propyl 4-vinylbenzoate, 2-[2-(2-methoxyethoxy)ethoxy]ethyl 4-vinylbenzoate (0.50 g, 1.7 mmol) and AIBN (0.3 mmol) to give 0.39 g of a highly viscous oil (yield: 56%).

Average molecular weight (GPC): ca. 6100 g/mol.

IR (neat): 2927m, 2869m, 1711s, 1650w, 1607m, 1573w, 1507w, 1451m, 1418m, 1373m, 1366m, 1352m, 1307m, 1270s, 1197m, 1179m, 1098s, 1029m, 1016m, 998w, 985w, 940m, 853m, 772m, 707m, 683m.

$^{13}$C-NMR: 166.1 (s); 165.3 (s); 149.3 (s, br.); 131.7 (d); 129.6 (d, br.); 128.2 (d, br.); 124.3 (d); 71.9 (t); 70.6 (t); 70.6 (t); 69.2 (t); 68.0 (t); 64.0 (t); 62.9 (d); 59.0 (q); 53.3 (t); 41.7 (t); 40.7 (d, br.); 33.1 (s); 21.6 (d); 29.8 (q); 20.7 (q); 20.1 (q); 19.9 (q).

Example 7

Release on a Perfuming Ingredient from Buffered Aqueous Solution Containing a Non-Ionic Surfactant and a Polymer According to the Invention An alkaline buffer solution containing 1% by weight of a non-ionic surfactant was prepared by dissolving two borate buffer tablets pH=9.2 and 2.24 g of Triton® X100 (origin: Union Carbide) in a mixture of 160 ml water and 40 ml of acetonitrile. To determine the exact pH value of the final reaction solution, 10 ml of the buffer were diluted with 2 ml of acetonitrile (to give a mixture of water/acetonitrile 2:1) and the pH values measured to be 10.5.

50 µl of a 0.25 M solution of the test compound in THF, were added to 5 ml of the above mentioned alkaline buffer (water/acetonitrile 4:1) and diluted with 1 ml of acetonitrile (to give a final mixture of water/acetonitrile 2:1). The sample was left stirring at room temperature for 3 day, then extracted with 1 ml of heptane and left decanting for 30 min. The heptane phase (0.5 µl) was injected three times into a Carlo Erba MFC 500 gas chromatograph equipped with a Fisons AS 800 autosampler and a J&W Scientific DB1 capillary column (30 m, 0.32 mm i.d.) at 70° C. for 10 min then to 260° C. (10° C./min), helium pressure 50 kPa, injection temperature 250° C., detector temperature 280° C. The amount of released damascone was determined by external standard calibration from five different concentrations in heptane, using the average of five injections for each calibration point. The results are summarized in the following table:

| Compound of Example | Amount of damascone released (in mol-%) |
|---|---|
| 6b) | 9 |
| 6d) | 9 |
| 6e) | 15 |

Whereas the compounds listed in the table were found to be stable in acidic medium, δ-damascone was released in all experiments under alkaline conditions. The results demonstrate that the rate of damascone released can be adapted to the particular needs of the final application by small variations of the precursor structure such as an increasing amount of a hydrophilic co-monomer incorporated in the polymer backbone.

Example 8

A Fabric Softener Base Containing a Compound of Formula (I)

A fabric-softener base was prepared by admixing the following ingredients:

| Ingredients | Parts by weight |
|---|---|
| Stepantex VK 90 diester quat[1] | 16.5 |
| Calcium chloride | 0.2 |
| Deionised Water | 81.8 |
| Total | 100 |

[1]origin: Stepan Europe, France

The compound to be tested was added to 35 g of fabric-softener base above in an amount ranging between 0.15 and 1 mmole. After a vigorous stirring the mixture was poured in the fabric-softener compartment of a Miele Novotronic W900-79 CH washing machine.

Then, 17 small terry towels (18×18 cm, about 30 g each) and 2.3 kg of large cotton towels (11 towels of 50×70 cm) were washed at 40° C. using the short cycle program and 136 g Henkel "ECE Colour fastness Test Detergent 77" unperfumed detergent At the end of the wash, the 17 small terry towels were dried in a drying room for 24 hours and then packed loosely in aluminium foil and evaluated by a 20 people panel 24 hours, 3 days and 7 days after the wash.

Each panelist was asked to rate the various terry towels tested on an intensity scale of 1 to 7 (1: no odor, 2: weak odor, 3: slightly weak odor, 4: medium odor, 5: slightly strong odor, 6: strong odor, 7: very strong odor).

As reference was used a fabric-softener base containing 1 mmole of pure alpha-damascone tested through the same process.

The results are summarized in the following tables for different perfuming enones:

1) α-Damascone Versus its Derivatives for Formula (I):

| Tested molecule | Quantity[1] | mmol[2] | Average intensity[3] |
|---|---|---|---|
| 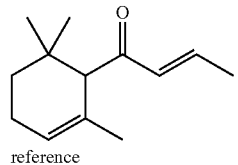 reference | 0.55<br>0.2 | 1.0<br>0.365 | 2.8<br>2.7 |
| 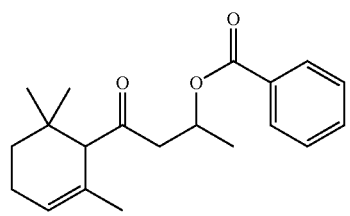 | 0.90<br>0.30<br>0.15 | 1.0<br>0.334<br>0.167 | 4.7<br>4.4<br>4.1 |
| 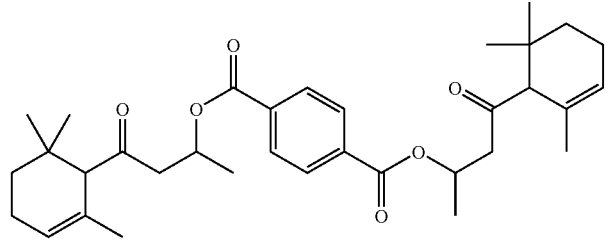 | 0.79 | 0.5 | 5.0 |
| 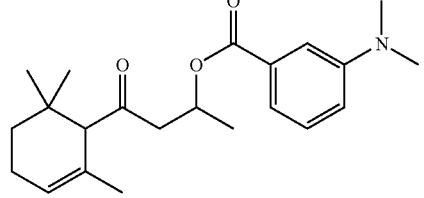 | 1.02 | 1.0 | 3.9 |
| 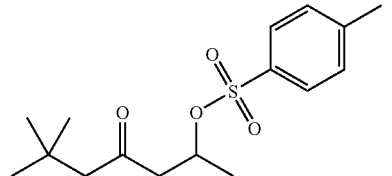 | 1.04 | 1.0 | 4.5 |

-continued
| Tested molecule | Quantity[1] | mmol[2] | Average intensity[3] |
|---|---|---|---|
| 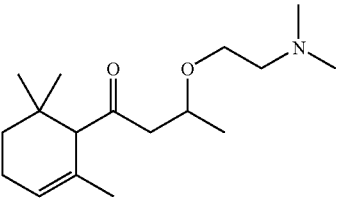 | 0.80 | 1.0 | 3.3 |
| 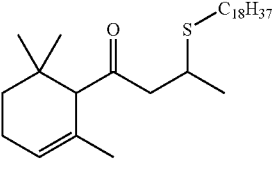 | 1.37 | 1.0 | 3.4 |
| 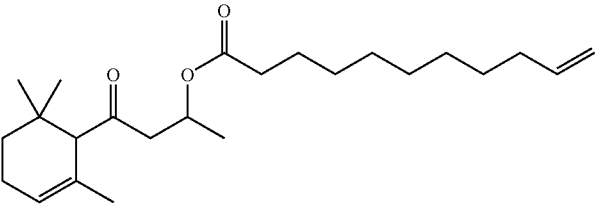 | 1.08 | 1.0 | 4.5 |
| 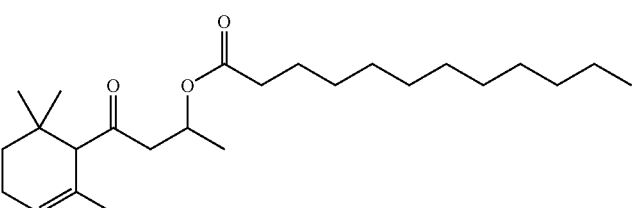 | 1.12 | 1.0 | 4.1 |
| 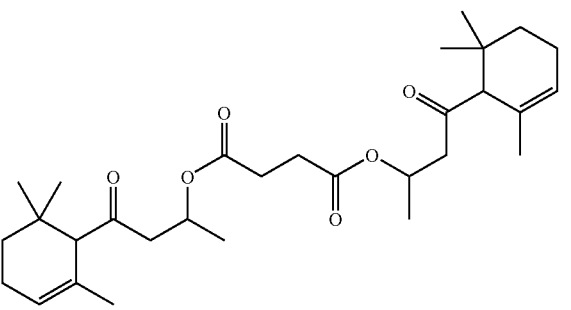 | 0.72 | 0.5 | 4.0 |
[1] quantity added into the 35 g of the fabric-softener base, in parts by weight
[2] milli moles added into the 35 g of the fabric-softener base
[3] average of the odor intensity of the dry fabric in the period ranging from one day to seven days after the wash 2) δ-Damascone Versus its Derivatives for Formula (I):
| Tested molecule | Quantity[1] | mmol[2] | Average intensity[3] |
|---|---|---|---|
| 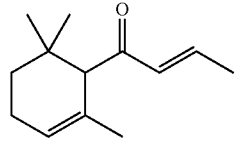 Reference | 0.55% | 1.0 | 3.2 |
| 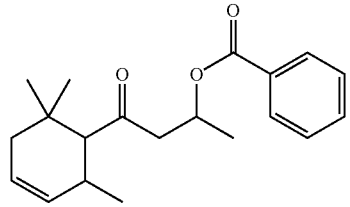 | 0.90% | 1.0 | 4.5 |
| 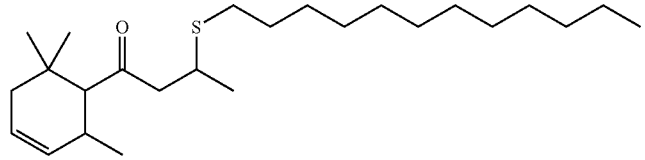 | 1.13 | 1.0 | 4.5 |
| 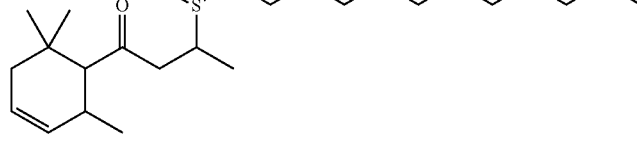 | 1.17 | 1.0 | 4.6 |
| 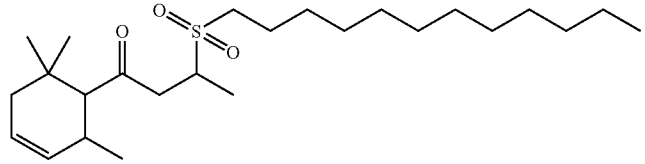 | 1.22 | 1.0 | 4.2 |
3) Dynascone® (Origin: Firmenich SA, Switzerland) Versus a Derivative for Formula (I):
| Tested molecule | Quantity[1] | mmol[2] | Average intensity[3] |
|---|---|---|---|
| 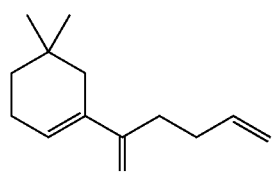 Reference | 0.55 | 1.0 | 3.3 |
| 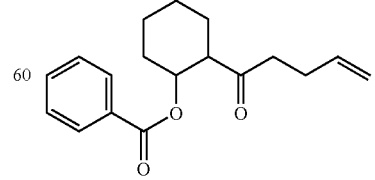 | 0.89 | 1.0 | 5.4 |

4) 1-(2,2,3,6-tetramethyl-1-cyclohexyl)-2-buten-1-one (Origin: Firmenich SA, Switzerland) Versus a Derivative for Formula (I):

| Tested molecule | Quantity[1] | mmol[2] | Average intensity[3] |
|---|---|---|---|
| 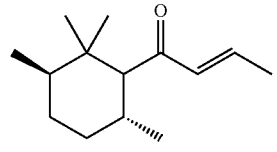 Reference | 0.59 | 1.0 | 3.3 |
| 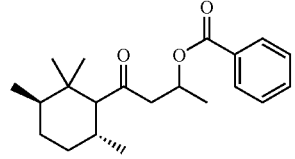 | 0.54 | 0.58 | 3.8 |

5) 1-(2,2,3-trimethyl-1,3-cyclohexadien-1yl)-2-buten-1-one Versus a Derivative for Formula (I):

| Tested molecule | Quantity[1] | mmol[2] | Average intensity[3] |
|---|---|---|---|
| 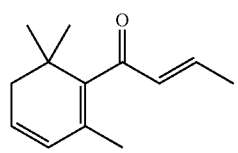 Reference | 0.54 | 1.0 | 3.4 |
| 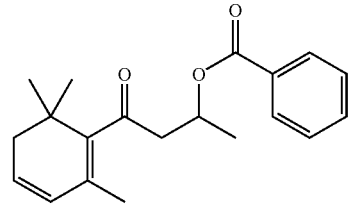 | 0.92 | 1.0 | 4.1 |

Example 9

A Granular Fabric Detergent Base Containing a Compound of Formula (D)

2 Mmoles of compound to be tested (or 0.001 mole for terephthalate derivative) were added to 100 g of Henkel "ECE Colour fastness Test Detergent 77" unperfumed detergent. After mixing, the new detergent base was poured in the powder compartment of a Miele Novotronic W900-79 CH washing machine. Fabric-softener was not used. Then, 17 small terry towels (18 cm×18 cm, about 30 g each) and 2.3 kg of large cotton towels (11 towels of 50×70 cm) were washed at 40° C. using the short cycle program Drying, storage and olfactive evaluation were performed as described in example 8) and the results are summarized in the following tables:

1) α-Damascone Versus its Derivatives for Formula (I):

| Tested molecule | Quantity[1] | mmol[2] | Average intensity[3] |
|---|---|---|---|
| 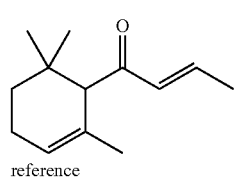 reference | 0.38 | 2.0 | 2.3 |
| 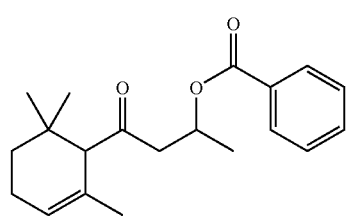 | 0.63 | 2.0 | 4.6 |

| Tested molecule | Quantity[1] | mmol[2] | Average intensity[3] |
|---|---|---|---|
| (structure) | 0.55 | 1.0 | 3.2 |
| (structure) | 0.56 | 2.0 | 2.8 |
| (structure) | 0.75 | 2.0 | 4.6 |
| (structure) | 0.78% | 2.0 | 4.0 |
| (structure) | 0.50 | 1.0 | 4.6 |

[1] quantity added into the 100 g of the fabric-detergent base, in parts by weight
[2] milli moles added into the 100 g of the fabric-detergent base
[3] average of the odor intensity of the dry fabric in the period ranging from one day to seven days after the wash 2) δ-Damascone Versus its Derivatives for Formula (I):

| Tested molecule | Quantity[1] | mmol[2] | Average intensity[3] |
|---|---|---|---|
| 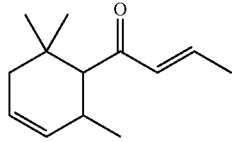 Reference | 0.39 | 2.0 | 2.6 |
| 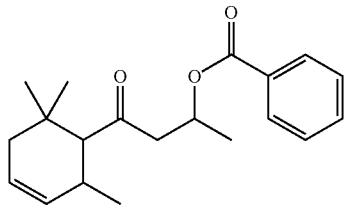 | 0.63 | 2.0 | 4.4 |
| 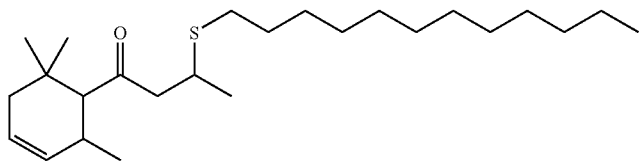 | 0.79 | 2.0 | 3.2 |
| 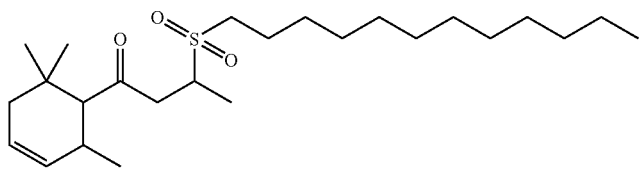 | 0.53 | 1.25 | 3.6 |

What is claimed is:

1. A perfuming composition or perfumed article comprising as active ingredient at least one compound of formula (I):

 (I)

wherein:
 a) w represents 1;
 b) n represents 1;
 c) m represents an integer from 1 to 4;
 d) P represents a radical susceptible of generating an odoriferous α,β-unsaturated ketone, aldehyde or carboxylic ester and is (P-1), (P-2), (P-3), (P-5), (P-6) or (P-7) as represented by the formula

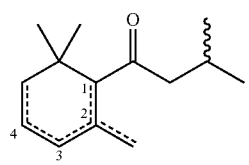 (P-1)

-continued

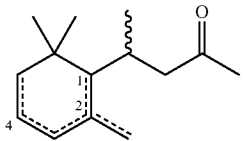 (P-2)

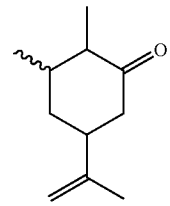 (P-3)

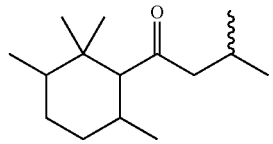 (P-5)

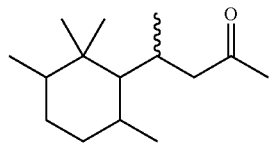 (P-6)

-continued

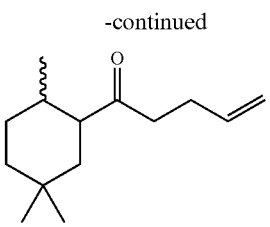
(P-7)

in which the wavy line indicates the location of the bond between the P and X, and the dotted lines represent a single or double bond;

e) X represents a functional group selected from the group consisting of the formulae ii), iv), viii) or ix):

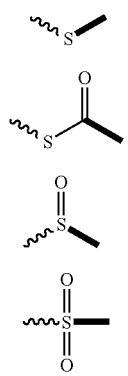

ii)

iv)

viii)

ix)

in which formulae the wavy lines are as defined previously and the bold lines indicate the location of the bond between the X and G;

f) G represents a multivalent radical (with a m+1 valence) derived from an aryl radical, optionally substituted, or a divalent cyclic, linear or branched alkyl, alkenyl, alkadienyl or alkylbenzene hydrocarbon radical having from 6 to 22 carbon atoms, or a tri-, or tetra-cyclic, linear or branched alkyl, alkenyl, alkadienyl or alkylbenzene hydrocarbon radical having from 1 to 22 carbon atoms, the hydrocarbon radical being optionally substituted and containing from 1 to 10 functional groups selected from the group consisting of ether, ester, ketone, amine, quaternary amines and amides; with optional substituents of G being halogen atoms, $NO_2$, $OR^6$, $NR^6_2$, $COOR^6$ or groups, with $R^6$ representing a $C_1$ to $C_{15}$ alkyl or alkenyl group; and g) Q represents a hydrogen atom.

2. A perfuming composition or perfumed article according to claim 1, wherein in formula (I):

m represents 1 or 2;

P represents a radical of the formulae (P-1), (P-2), (P-3), (P-5), or (P-6)

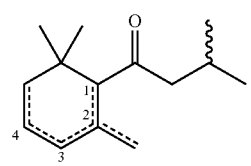
(P-1)

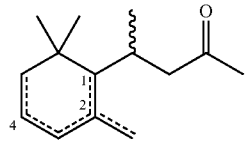
(P-2)

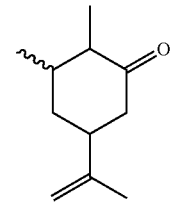
(P-3)

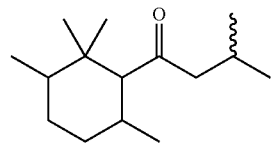
(P-5)

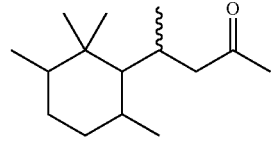
(P-6)

G represents a bivalent or trivalent radical derived from an aryl radical, optionally substituted, or a divalent cyclic, linear or branched alkyl, alkenyl, alkadienyl or alkylbenzene hydrocarbon radical having from 8 to 22 carbon atoms, or a trivalent cyclic, linear or branched alkyl or alkenyl hydrocarbon radical having from 1 to 22 carbon atoms, the hydrocarbon radical being optionally substituted and containing from 1 to 5 functional groups selected from the group consisting of ether, ester, ketone, amine, quaternary amines and amides; possible substituents of 0 are halogen atoms, $NO_2$, $OR^6$, $NR^6_2$, $COOR^6$ or $R^6$ groups, $R^6$ representing a $C_1$ to $C_{15}$ alkyl or alkenyl group.

3. A perfuming composition or perfumed article according to claim 1, wherein n is 1;

m represents 1 or 2;

P represents a radical of the formulae (P-1), (P-2), (P-3), (P-5), or (P-6)

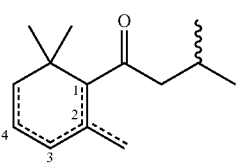
(P-1)

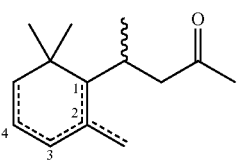
(P-2)

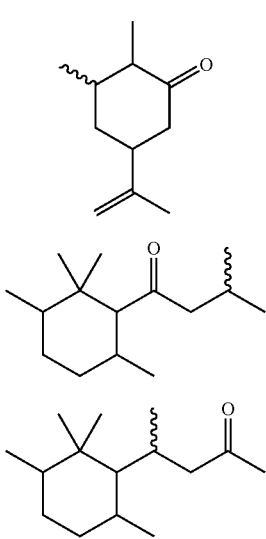

G represents a bivalent radical derived from a linear or branched alkyl or alkenyl, hydrocarbon radical having from 8 to 15 carbon atoms; or G represents a trivalent radical derived from a linear or branched alkyl hydrocarbon radical having from 2 to 10 carbon atoms.

4. A perfuming composition or perfumed article according to claim 1, wherein n is 1;

m represents 1 or 2;

P represents a radical of the formulae (P-1), (P-2), (P-5), or (P-6):

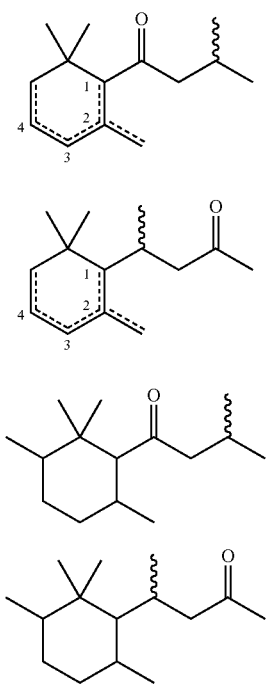

and

G represents a bivalent or trivalent radical derived from a linear or branched alkyl or alkenyl, hydrocarbon radical having from 8 to 15 carbon atoms.

5. A perfuming composition or perfumed article according to claim 4, wherein in the compound of formula I:

X=—S—;

G=a divalent cyclic, linear or branched alkyl, alkenyl, alkadienyl or alkylbenzene hydrocarbon radical having from 8 to 22 carbon atoms, or a trivalent cyclic, linear or branched alkyl or alkenyl hydrocarbon radical having from 1 to 22 carbon atoms, the hydrocarbon radical being optionally substituted; and m=1.

6. A perfumed article according to claim 1, in the form of a solid or liquid detergents, a fabric softener, a perfume, cologne or after-shave, a perfumed soap, a shower or bath gel, mousse, oil or salt, a hygiene product or hair care product, a body-care product, a deodorant or antiperspirant, an air freshener, a cosmetic preparation, a fabric refresher, an ironing water, a paper, a wipe or a bleach.

7. A method to improve, enhance or modify the odor of a perfumed article or perfuming composition, which method comprises adding to the article or composition a fragrance effective amount of a compound of formula (I), as defined in claim 1.

8. A method for the perfuming of a surface, characterized in that the surface is treated in the presence of a compound of formula (I) as defined in claim 1.

9. A method for intensifying or prolonging the diffusion effect of an odoriferous ingredient on a surface, characterized in that the surface is treated in the presence of a compound of formula (I) as defined in claim 1.

10. A perfuming composition or perfumed article comprising a compound of formula I according to claim 1 that includes a solvent of the type that is commonly used in perfumery.

11. The perfuming composition or perfumed article of claim 10 wherein the solvent is dipropyleneglycol, diethyl phthalate, isopropyl myristate, benzyl benzoate, 2-(2-ethoxyethoxy)-1-ethanol or ethyl citrate.

12. A perfuming composition or perfumed article according to claim 1, wherein in the compound of formula I:

P = (P-1)

X=—S—;

G=$C_{12}H_{24}$; and m=1.

13. A perfuming composition or perfumed article according to claim 1, wherein in the compound of formula I:

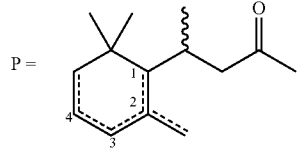
(P-2)

X=—S—;

G=$C_{12}H_{24}$; and m=1.

14. A perfuming composition or perfumed article according to claim 1, wherein in the compound of formula I:

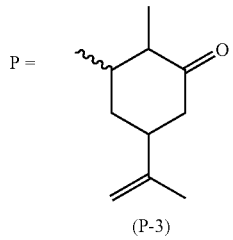
(P-3)

X=—S—;

G=$C_{12}H_{24}$; and m=1.

15. A perfuming composition or perfumed article according to claim 1, wherein in the compound of formula I:

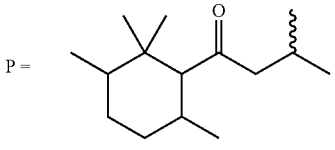
(P-5)

X=—S—;

G=$C_{12}H_{24}$; and m=1.

16. A perfuming composition or perfumed article according to claim 1, wherein in the compound of formula I:

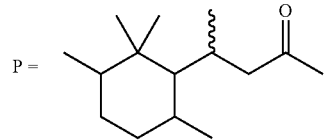
(P-6)

X=—S—;

G=$C_{12}H_{24}$; and m=1.

* * * * *

UNITED STATES PATENT AND TRADEMARK OFFICE
CERTIFICATE OF CORRECTION

PATENT NO.       : 7,723,286 B2
APPLICATION NO.  : 10/852754
DATED            : May 25, 2010
INVENTOR(S)      : Fehr et al.

It is certified that error appears in the above-identified patent and that said Letters Patent is hereby corrected as shown below:

Column 2:
Lines 55-57, formula (I) and insert the following:

$$-\left[\left[\left[P\sim\!\!\!\sim\!X\text{—}\right]_m\text{—}G'''\right]_n{}^{\prime\prime\prime}Q\right]_w-$$

Column 12:
Line 34, delete formula (I') and insert the following:

$$-\left[P\sim\!\!\!\sim\!X\text{—}\right]_m\text{—}G'''''Q-$$

Column 13:
Line 59, delete formula (I') and insert the following:

$$-\left[P\sim\!\!\!\sim\!X\text{—}\right]_m\text{—}G'''''Q-$$

Column 14:
Line 9, delete formula (I') and insert the following:

$$-\left[P\sim\!\!\!\sim\!X\text{—}\right]_m\text{—}G'''''Q-$$

Column 41:
Lines 43-45, delete formula (I') and insert the following:

$$-\left[\left[\left[P\sim\!\!\!\sim\!X\text{—}\right]_m\text{—}G'''\right]_n{}^{\prime\prime\prime}Q\right]_w-$$

Signed and Sealed this

Thirteenth Day of July, 2010

David J. Kappos
*Director of the United States Patent and Trademark Office*

Column 44:
Line 41, after "substituents of", delete "0" and insert -- G --